(12) United States Patent
Souza et al.

(10) Patent No.: US 9,909,116 B2
(45) Date of Patent: *Mar. 6, 2018

(54) SYSTEMS AND METHODS FOR MAGNETIC GUIDANCE AND PATTERNING OF MATERIALS

(71) Applicant: William Marsh Rice University, Houston, TX (US)

(72) Inventors: Glauco R Souza, Houston, TX (US); Renata Pasqualini, Houston, TX (US); Wadih Arap, Houston, TX (US); Thomas Charles Killian, Houston, TX (US); Robert M. Raphael, Houston, TX (US); Daniel Joshua Stark, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 676 days.

This patent is subject to a terminal disclaimer.

(21) Appl. No.: 14/331,377

(22) Filed: Jul. 15, 2014

(65) Prior Publication Data

US 2014/0322784 A1    Oct. 30, 2014

Related U.S. Application Data

(60) Division of application No. 13/070,873, filed on Mar. 24, 2011, now Pat. No. 8,815,231, which is a continuation of application No. PCT/US2009/058473, filed on Sep. 25, 2009.

(Continued)

(51) Int. Cl.
*C12N 5/00* (2006.01)
*C12N 13/00* (2006.01)
(Continued)

(52) U.S. Cl.
CPC ............... *C12N 13/00* (2013.01); *B82Y 5/00* (2013.01); *C12M 35/06* (2013.01);
(Continued)

(58) Field of Classification Search
CPC .................................................. C12N 5/0062
See application file for complete search history.

(56) References Cited

FOREIGN PATENT DOCUMENTS

| EP | 09816948.5 | 5/2013 |
|---|---|---|
| WO | 2005003332 | 1/2005 |
| WO | 2006060171 | 6/2006 |

OTHER PUBLICATIONS

Ito et al., Construction and Harvest of Multilayered Keratinocyte Sheets USing Magnetite Nanoparticles and Magnetic Force, Tissue Engineering, vol. 10, No. 5/6, 2004.

(Continued)

*Primary Examiner* — Rosanne Kosson
(74) *Attorney, Agent, or Firm* — Boulware & Valoir

(57) ABSTRACT

Systems and methods generally useful in medicine, cellular biology, nanotechnology, and cell culturing are discussed. In particular, at least in some embodiments, systems and methods for magnetic guidance and patterning of cells and materials are discussed. Some specific applications of these systems and methods may include levitated culturing of cells away from a surface, making and manipulating patterns of levitated cells, and patterning culturing of cells on a surface. Specifically, a method of culturing cells is presented. The method may comprise providing a plurality of cells, providing a magnetic field, and levitating at least some of the plurality of cells in the magnetic field, wherein the plurality of cells comprise magnetic nanoparticles. The method may also comprise maintaining the levitation for a time sufficient to permit cell growth to form an assembly.

12 Claims, 24 Drawing Sheets

Related U.S. Application Data

(60) Provisional application No. 61/099,966, filed on Sep. 25, 2008.

(51) Int. Cl.
  *B82Y 5/00* (2011.01)
  *C12M 1/42* (2006.01)

(52) U.S. Cl.
  CPC ........ *C12N 5/0062* (2013.01); *C12N 2529/00* (2013.01); *C12N 2533/10* (2013.01)

(56) References Cited

OTHER PUBLICATIONS

Souza Glauco R et al, "Three-dimensional tissue culture based on magnetic cell levitation", Nature Nanotechnology, Apr. 2010, 5(4): 291-296.
Lin Ruei-Zhen et al, "Recent advances in three-dimensional multicellular spheroid culture for biomedical research", Biotechnology Journal, 2008, 3(9-10): 1172-1184.
Lin Ruei-Zeng et al, "Magnetic reconstruction of three-dimensional tissues from multicellular spheroids" Tissue Engineering. Part C, Methods Sep. 2008, 14(3): 197-205.
Jurgons et al. "Drug loaded magnetic nanoparticles for cancer therapy" J. Phys.: Conds. Mat., 2006, 18:s2893-s2902.
Ino et al. "Cell patterning unsing magnetite nanoparticles and magnetic forces" Biotech. Bioeng., 2007, 97:1309-1317.
Alsberg, "Magnetically-Guided Self-Assembly of Fibrin Matrices with Ordered Nano-Scale Structure for Tissue Engineering", Tiss. Eng. 2006 12:3247-3255.

Figure 7
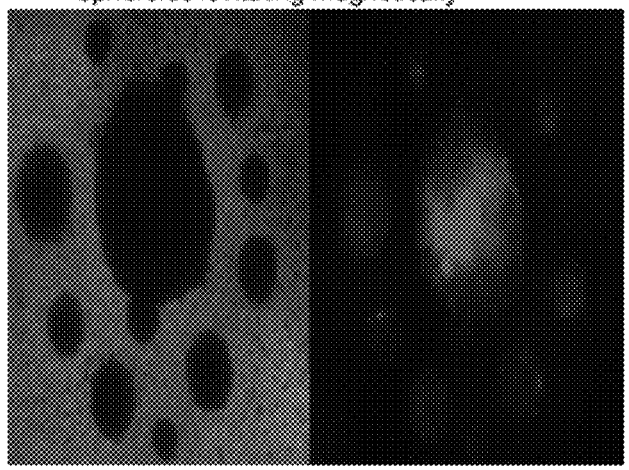
Human Astrocyte spheroids, t = 36 hours
Spheroids levitating magnetically
Human Astrocytes, t = 0
Cells magnetically levitated (NOT at the bottom)
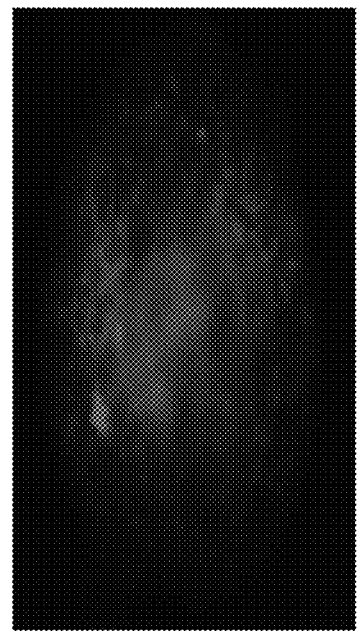
Human Astrocytes Spheroid
* Red = mCherry ~ 6 mm Figure 18
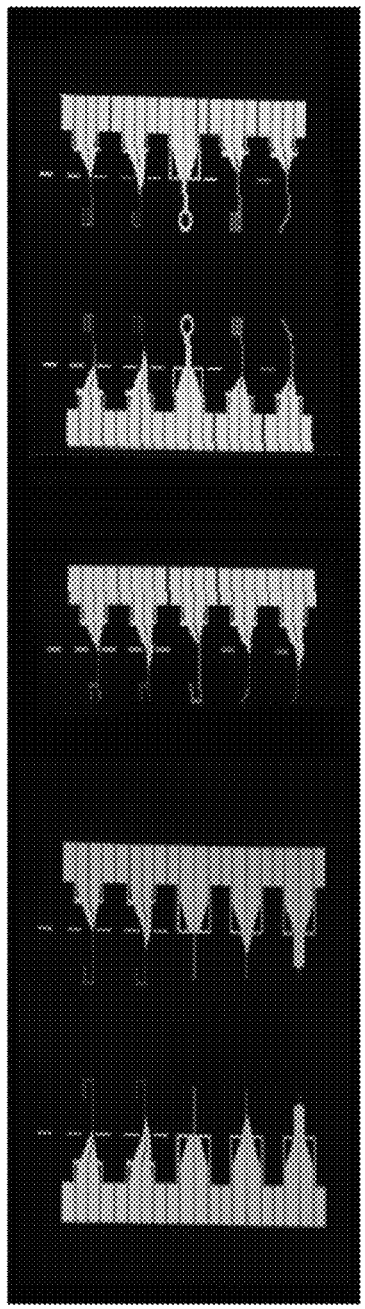
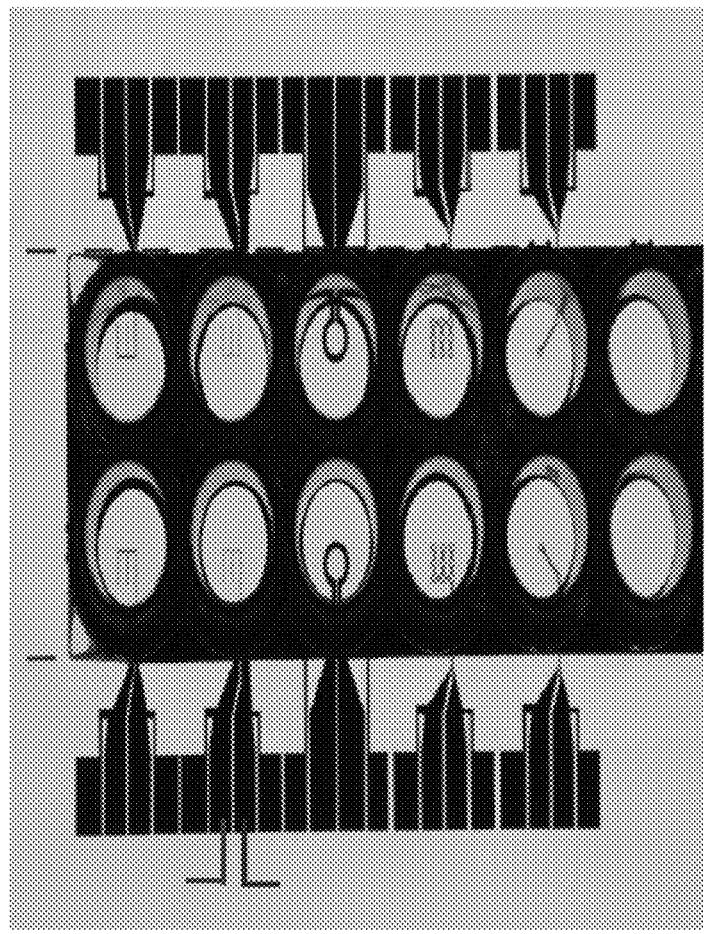

Figure 23
RGD-4C (targeted)
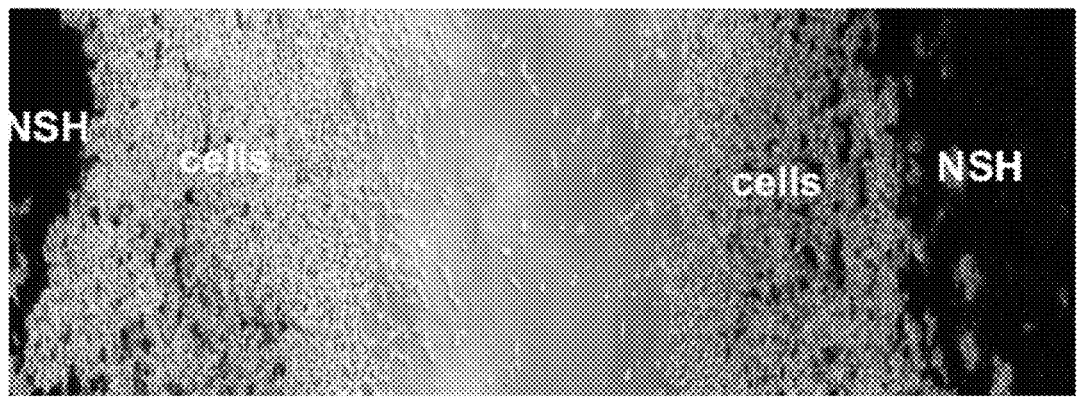
fd-tet (non-targeted)
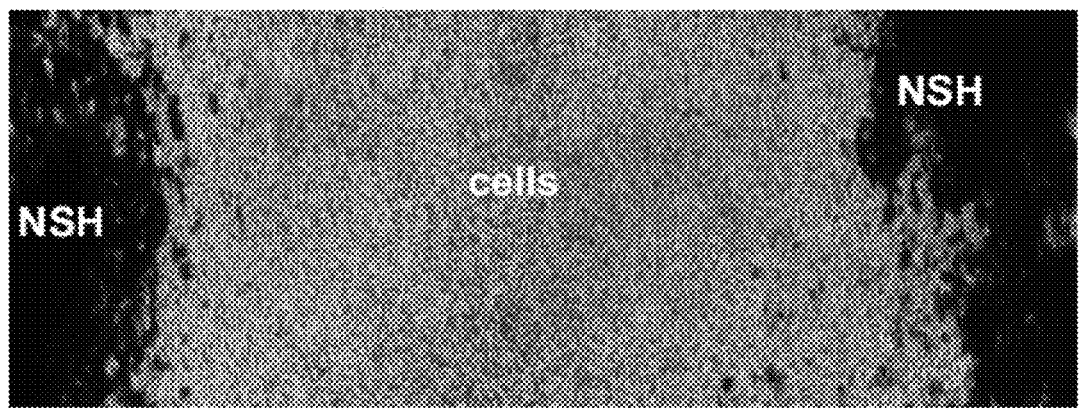
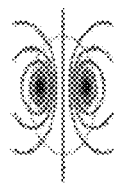

Figure 24
Brightfield
Magnet    No Magnet
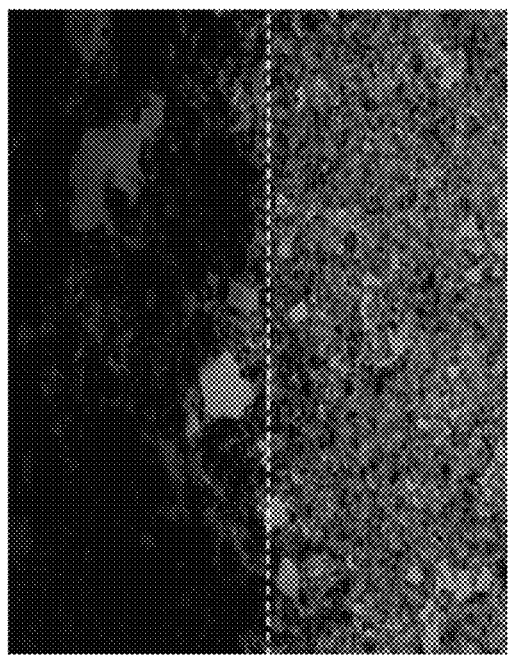
GFP Fluorescence
Magnet    No Magnet
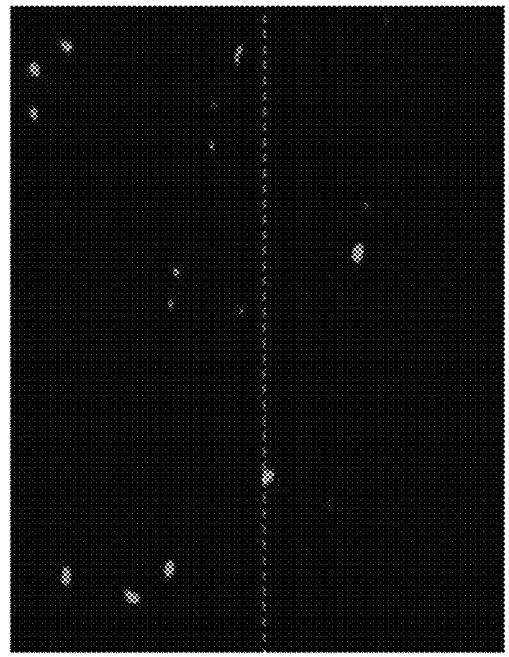
5x Magnification

SYSTEMS AND METHODS FOR MAGNETIC GUIDANCE AND PATTERNING OF MATERIALS

FEDERALLY SPONSORED RESEARCH STATEMENT

This invention was made with government support under NSF Grant No. DGE-0237081 and Army Medical Research and Material Command Grant No. W81XWH-06-1-0775. The government has certain rights in the invention.

CROSS-REFERENCE TO RELATED APPLICATIONS

This application is a divisional of U.S. application Ser. No. 13/070,873, filed Mar. 24, 2011, which is a continuation of International Application PCT/US2009/58473, filed Sep. 25, 2009, which claims benefit of U.S. Provisional Patent Application Ser. No. 61/099,966, filed Sep. 25, 2008, all of which are incorporated by reference.

BACKGROUND

The present disclosure relates generally to systems and methods useful in medicine, cellular biology, nanotechnology, and cell culturing. In particular, at least in some embodiments, the present disclosure relates to systems and methods for magnetic guidance and patterning of cells and materials. Some specific applications of these systems and methods are levitated culturing of cells away from a surface, making and manipulating patterns of levitated cells, and patterning culturing of cells on a surface.

As interest in nanotechnology, materials, and cellular biology has grown, it has become evident that a limitation is the ability to control and manipulate the pattern of cells and materials which are useful for cellular biology and medicine (such as cell culturing, tissue engineering, stem cell research, drug and nanoparticle delivery, bio-sensors, and gene delivery), molecular and bioelectronics, and the construction of complex materials.

During development of living organisms, structure and order in the form of patterns naturally emerge through mechanisms that are still not fully understood. If one wants to study or replicate living tissue in an artificial environment, it is critical to be able to reproduce natural patterns. The ability to engineer and manually control the patterns of living cells, especially in three-dimensions and on surfaces, will enable many bioengineering and medical applications.

Cell culturing is an essential tool in many areas of biotechnology, such as stem cell research, tissue engineering, and drug discovery. Traditional cell culturing in Petri dishes produces two-dimensional (2D) cell growth with gene expression, signaling, and morphology that can differ from conditions in living organisms, and thus compromise clinical relevancy. Certain limitations of traditional cell culturing in recapitulating the attributes of tissues in living organisms may result from their 2D nature. While rotating bioreactors or protein-based gel environments have been developed in attempts to allow three-dimensional (3D) cell culturing, broad application of such methods has been severely hampered by high-cost or complexity. Thus, a platform technology to enable 3D cell culturing is still an unmet need.

In many cases, an ideal cell culturing environment is one that promotes fast and robust growth of healthy cells, in which the cell morphology and function are dominated by cell-cell interactions, cell-specific signaling, and/or experimental control variables, rather than the properties of the artificial culturing medium. Often, it is desirable to grow cells that resemble in substantially every way cells grown in living organisms, including gene expression, functional characteristics of differentiated cells, and the formation of an extracellular matrix. Cost and scalability of production are also critical considerations as far as the application potential of such technologies.

Furthermore, as the use of nano-sized materials and cultured cells continue to develop, it is increasingly difficult to develop systems for safely manipulating and handling these entities. For example, regulatory agencies and good laboratory practices often attempt to minimize the amount of exposure of materials to external objects, so as to minimize contamination. Aside from such practices, the integrity of such materials may be compromised by such an exposure. Thus, devices which can manipulate nano-sized materials and cells and tissue without exposure to external objects may be desirable.

The features and advantages of the present disclosure will be readily apparent to those skilled in the art upon a reading of the description of the embodiments that follows.

SUMMARY

The present disclosure relates generally to systems and methods useful in medicine, cellular biology, nanotechnology, and cell culturing. In particular, at least in some embodiments, the present disclosure relates to systems and methods for magnetic guidance and patterning of cells and materials. Some specific applications of these systems and methods are levitated culturing of cells away from a surface, making and manipulating patterns of levitated cells, and patterning culturing of cells on a surface.

The present disclosure provides, in certain embodiments, a method for levitating a plurality of cells. The method may comprise providing a magnetic field. The method may also comprise levitating at least some of the plurality of cells in the magnetic field, wherein the plurality of cells comprise magnetic nanoparticles.

The present disclosure also provides, in some embodiments, a method of culturing cells. The method may comprise providing a plurality of cells. The method may also comprise providing a magnetic field. The method may also comprise levitating at least some of the plurality of cells in the magnetic field, wherein the plurality of cells comprise magnetic nanoparticles. The method may also comprise maintaining the levitation for a time sufficient to permit cell growth to form an assembly.

The present disclosure also provides, in other embodiments, a method of manipulating cells. The method may comprise providing a first plurality of cells. The method may also comprise providing a magnetic field. The method may also comprise levitating at least some of the first plurality of cells in the magnetic field, wherein the first plurality of cells comprise magnetic nanoparticles. The method may also comprise varying the magnetic field over time to manipulate at least a first portion of the first plurality of cells.

The present disclosure also provides, in particular embodiments, a method of preparing nanoparticles. The method may comprise providing a hydrogel comprising magnetic nanoparticles. The method may also comprise providing a magnetic field. The method may also comprise subjecting the hydrogel to the magnetic field.

The present disclosure also provides, in yet other embodiments, a system for levitating a plurality of cells. The system may comprise a magnetic field. The system may also comprise the plurality of cells, wherein the plurality of cells are disposed in the magnetic field, and the plurality of cells comprise magnetic nanoparticles.

The features and advantages of the present disclosure will be apparent to those skilled in the art. While numerous changes may be made by those skilled in the art, such changes are within the spirit of the disclosure.

DRAWINGS

Some specific example embodiments of the disclosure may be understood by referring, in part, to the following description and the accompanying drawings.

FIGS. 1A-C illustrate an example Au-MIO-phage hydrogel, according to certain embodiments of the disclosure. FIG. 1A is a vial of a MIO-containing hydrogel (indicated by arrow) in water. FIG. 1B displays a scheme of electrostatic interaction of nanoparticles (spheres) with phage (elongated structures). FIG. 1C illustrates an exemplary MRI image (T2-weighted) of purified hydrogel in solution, MIO-containing hydrogel (top panel), average T2*=76 ms and MIO-free hydrogel control (bottom panel), average T2*=253 ms.

FIG. 2 illustrates magnetic displacement of Au-MIO-phage, according to some embodiments of the disclosure.

FIGS. 3A-D illustrates magnetic-based levitated cell culturing with initial cell attachment, according to some embodiments of the disclosure, during incubation (FIG. 3A), after being washed (FIG. 3B), in a petri dish under a magnet (FIG. 3C) and cells forming multicellular structures (FIG. 3D).

FIG. 4A-C illustrates magnetic-based levitated cell culturing in the absence of cell attachment, according to certain embodiments of the disclosure. FIG. 4A shows an Au-MIO-phage incubated with suspended cells for 15 min. FIG. 4B shows phase contrast (left) and fluorescence photomicrographs (right) of levitated mCherry-expressing normal human astrocytes. FIG. 4C shows a magnified image of a spheroid.

FIG. 7 illustrates magnetically levitated human astrocytes, according to certain embodiments of the disclosure.

FIGS. 12A-C illustrate a comparison of assemblies of cells (FIG. 12A) created with magnetic levitation with a 2D assembly (FIG. 12B) and a mouse xenograft (FIG. 12C), according to certain embodiments of the disclosure.

FIGS. 13A-D illustrate manipulation of cells during cell culturing, including control of shape and position, co-culturing, and confrontation assay, according to embodiments of the disclosure. FIG. 13A illustrates calculated magnetic field patterns of ring magnets used for 3-D cell assembly in 13B. FIG. 13C illustrates brightfield and fluorescence photomicrograph of human glioblastoma cells (green; GFP-expressing cells) and normal human astrocytes (red; mCherry-labeled) cultured separately and then magnetically guided together (time=0). FIG. 13D illustrates confrontation between human glioblastoma cells and normal astrocytes in FIG. 13C.

Figure 14:
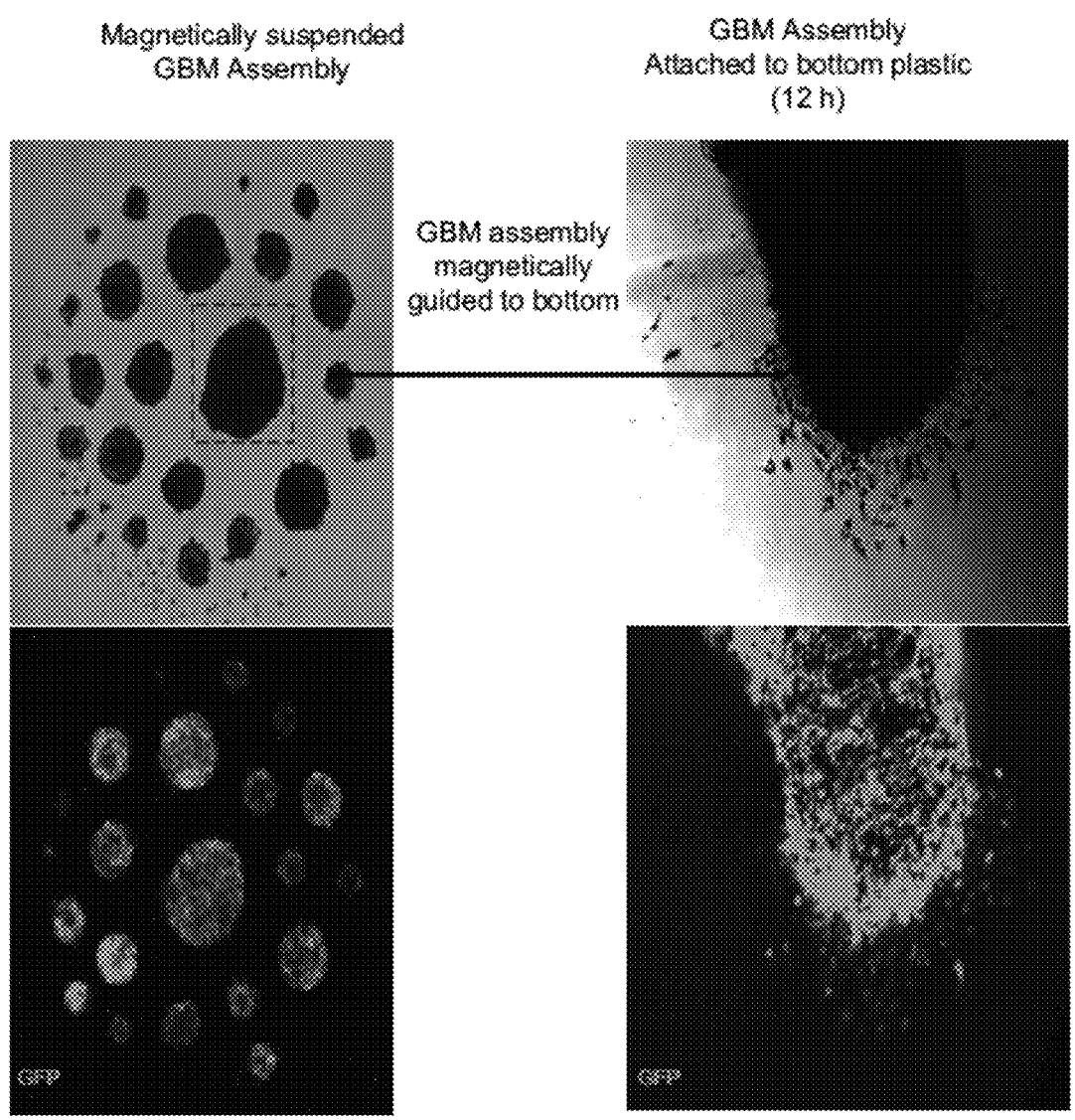

FIG. 14 illustrates an example of cell patterning on a surface, according to some embodiments of the disclosure.

Figure 15:
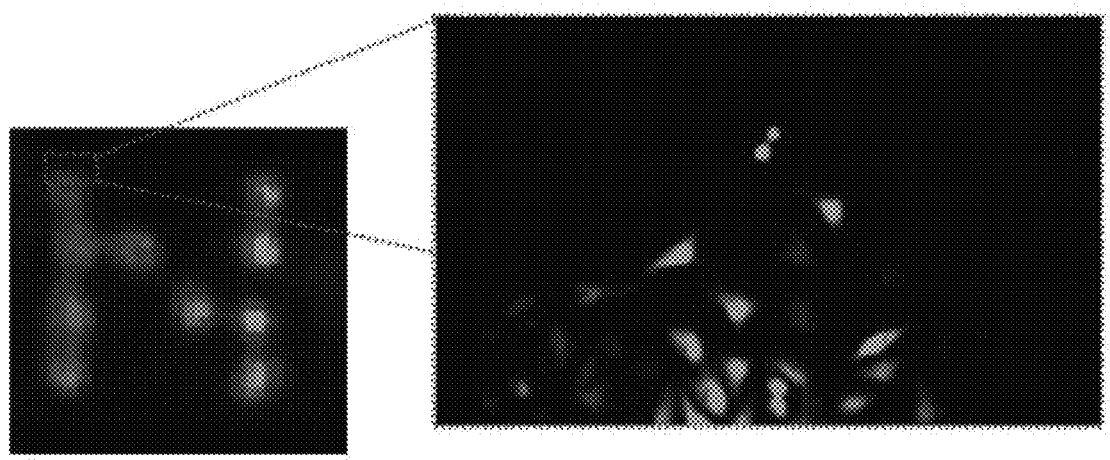

FIG. 15 illustrates an example of cell patterning on a surface, according to one embodiment of the disclosure.

Figure 16:
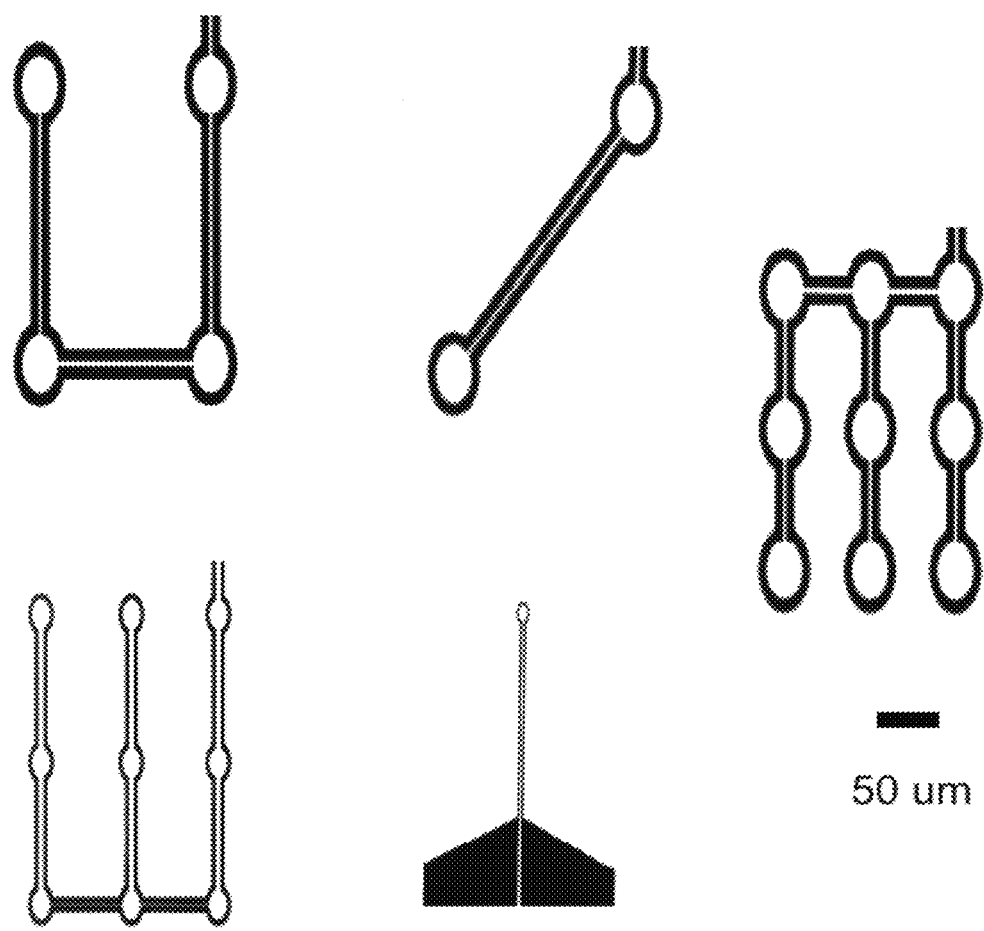

FIG. 16 illustrates sample lithographic patterns for making surface patterns of cells, according to embodiments of the disclosure.

Figure 17:
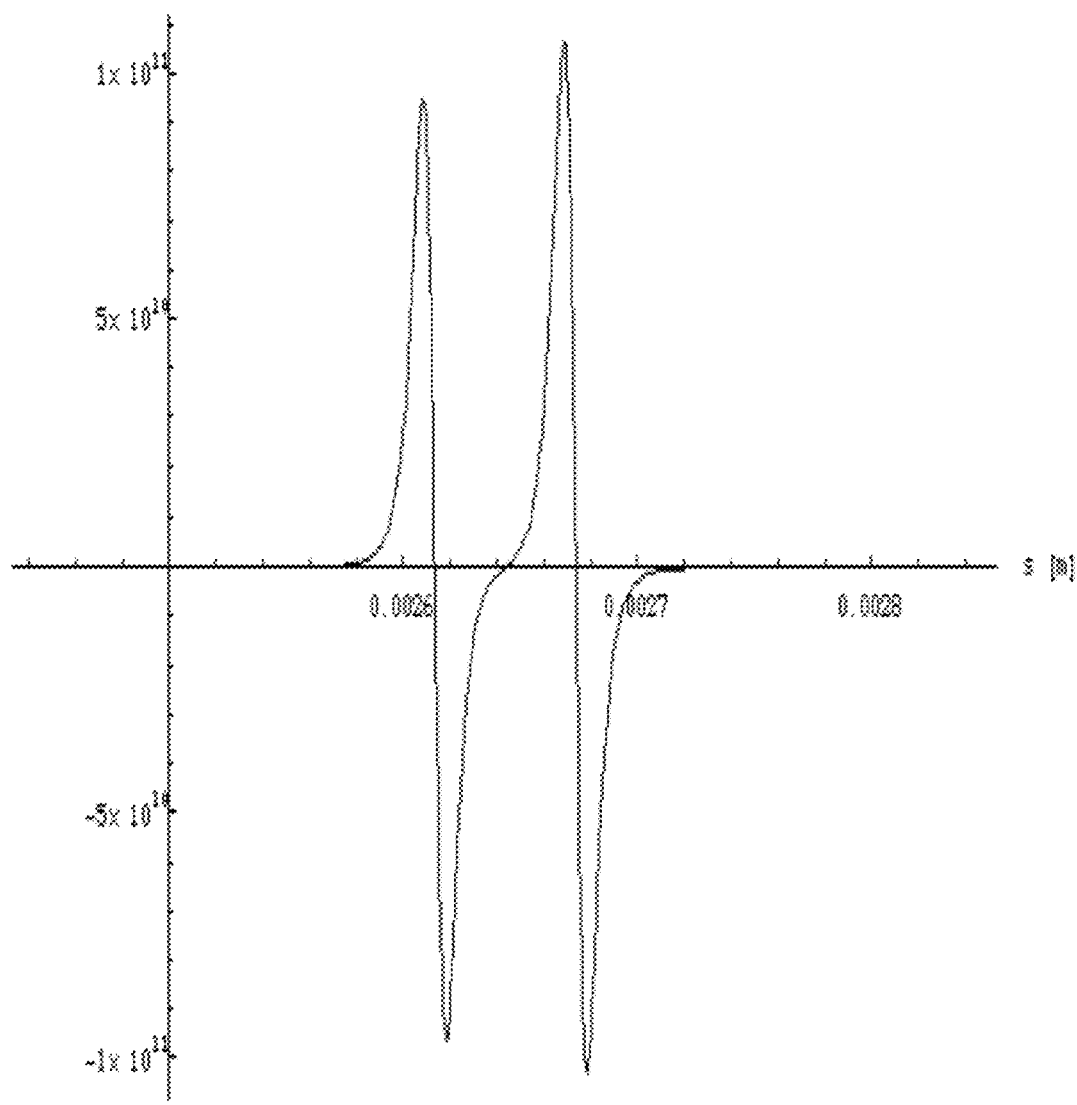

FIG. 17 illustrates sample magnetic force calculations, applicable to some embodiments of the disclosure.

FIG. 18 illustrates prototype microdevice construction for lithographically patterned wires, according to embodiments of the disclosure.

Figure 19:
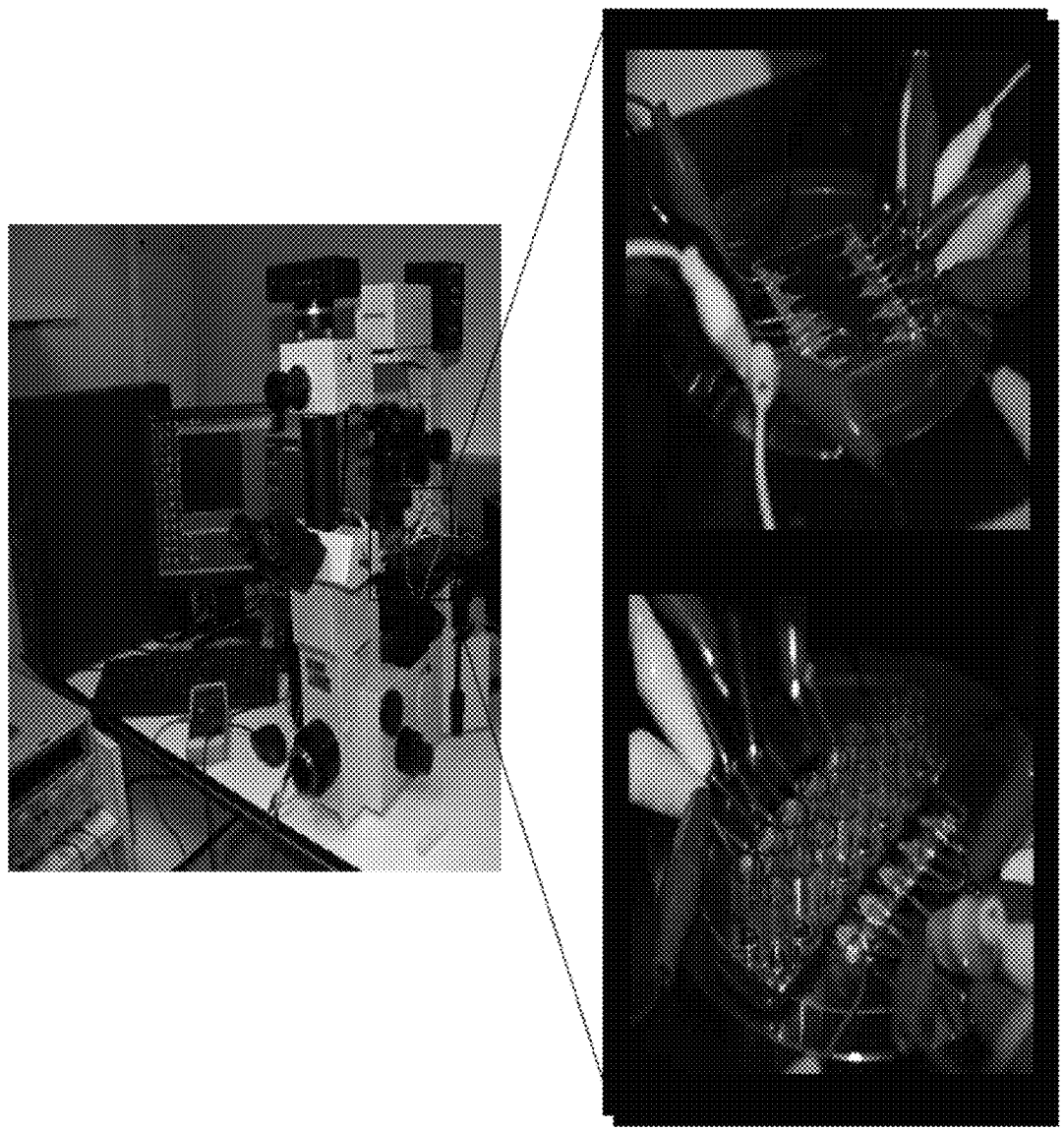

FIG. 19 illustrates a microscope set up and microchip device useful in some embodiments of the disclosure.

FIGS. 20A-B illustrate manipulation and surface patterning of neural stem cells with patterning microdevice, according to embodiments of the disclosure. FIG. 20A illustrates no current being applied. FIG. 20B illustrates cell assemblies displaced towards the Au wire pattern when a 4 A current is applied.

FIGS. 21A-B illustrate manipulation and patterning of Au-MIO-phage material without cells, according to embodiments of the disclosure. Both FIGS. 21A and 21B illustrate the sequences of no current being applied in the first frame, and the current ramped up to 4.0 A over an interval of 45 s.

Figure 22:

FIG. 22 illustrates a Au-MIO-phage gradient, according to embodiments of the disclosure.

FIG. 23 illustrates receptor-targeted cell patterning using magnetic field patterning of hydrogels, according to some embodiments of the disclosure.

FIG. 24 illustrates magnetic-guided gene transduction using Au-MIO-AAVP, according to embodiments of the disclosure.

While the present disclosure is susceptible to various modifications and alternative forms, specific example embodiments have been shown in the Figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

"Pattern," as used herein, refers to a pre-defined shape, position, location, and/or orientation, in either two or three dimensions.

"Manipulate," as used herein, refers to varying a pattern over time.

"Nanoparticles," as used herein, refers to particles with size ranges generally from about 0.1 nm to about 100 microns; in some embodiments, nanoparticles may have size ranges from about 5 to about 200 nm.

"Assembly," as used herein, refers to a grouping of one or more cells and any extracellular matrix or other substance which has tendency to remain in close proximity to the grouping.

"Magnetic nanoparticles," as used herein, refers to nanoparticles in which the saturation magnetization is at least about 0.001 emu/gram; in some embodiments, the saturation magnetization may be between about 10 to 200 emu/gram.

"Hydrogel," as used herein, refers to a material formed by incorporating any kind of bacteriophage (also referred to as a "phage") with nanoparticles. Different varieties of hydrogels may be indicated with different levels of specificity. Au-phage may be the most general form, referring to any kind of phage and any combination of nanoparticles, at least one kind of which is Au. Au—X-phage specifies that the nanoparticle described by X is also present. Specific phage varieties may also be specified.

"Au-MIO-phage," as used herein, refers to a material formed by incorporating any kind of bacteriophage with nanoparticles, at least one kind of which is Au and one kind of which is magnetic.

"Cell culturing," as used herein, generally refers to growing cells in a controlled environment. In many instances, the controlled environment is an artificial, laboratory environment, sometimes referred to as an in vitro environment.

As used herein, the term "altered in response to the magnetic field" and its derivatives includes any response of the systems of the present disclosure to the magnetic field, including, but not limited to, changes in shape, size, position, chemical environment, orientation of molecules and/or cells, as well as cellular events (in embodiments of the systems and methods of the present disclosure in which the systems and methods comprise one or more cells) such as, but not limited to, gene expression, signal transduction, changes in shape, position, orientation, and/or local chemical environment of the cells. Other responses of the systems of the present disclosure to magnetic fields may be recognized by one of ordinary skill in the art. Such responses are considered to be within the spirit of the present disclosure.

If there is any conflict in the usages of a word or term in this specification and one or more patent or other documents that may be incorporated herein by reference, the definitions that are consistent with this specification should be adopted for the purposes of understanding this disclosure.

The present disclosure relates generally to systems and methods useful in medicine, cellular biology, nanotechnology, and cell culturing. In particular, at least in some embodiments, the present disclosure relates to systems and methods for magnetic guidance and patterning of cells and materials. Some specific applications of these systems and methods are levitated culturing of cells away from a surface, making and manipulating patterns of levitated cells, and patterning culturing of cells on a surface.

The present disclosure generally combines magnetic fields and magnetic nanoparticles to provide a virtual platform or scaffold for controlling the pattern of cells and/or shape of assemblies of cells cultured in an artificial environment. In some embodiments, the present disclosure may also allow manipulation of cells, patterning of cells, and/or shaping of assemblies via variations in a magnetic field. In some embodiments, the methods of the present disclosure may be applied to pattern magnetic materials themselves to enable many useful applications pertaining to medicine, cellular biology, nanotechnology, and cell culturing. One of the many potential advantages of the devices and methods of the present disclosure, only some of which are herein disclosed, is that embodiments of the disclosure may allow cells and materials to be manipulated and patterned with great flexibility. In some embodiments, this may be done externally (without direct contact with solution being manipulated), which has compelling value for manipulating biological and molecular systems whose integrity can be easily compromised by contamination or handling.[18-24] In some embodiments, the inventive systems may be portable, relatively inexpensive, and easy to manufacture. Some embodiments of the disclosure may be coupled with many different modalities of optical microscopy and force microscopy.

The systems and methods of the present disclosure provide a number of other advantages over traditional systems and methods. For example, in certain embodiments, the systems and methods of the present disclosure may allow for the fabrication of a material without direct contact of external objects with the material. Such a contact-free fabrication may be accomplished, in part, by the use of magnetic fields and materials which respond to such magnetic fields. Furthermore, the systems and methods of the present disclosure, in certain embodiments, may allow for precise control of the mechanical forces placed upon a material during fabrication. Such control may be advantageous, for example, when the material comprises one or more cells which are sensitive to such mechanical forces, i.e. mechanosensitive cells. Such cells include, but are not limited to, stem cells. Additionally, in certain embodiments, the systems and methods of the present disclosure may allow for precise manipulation of the magnetic fields used in the systems and methods of the present disclosure, such as the ability to generate or remove such a magnetic field, increase or decrease the strength of such a magnetic field, or modulate such a magnetic field.

Embodiments of the present disclosure advantageously may provide 3D cell growth with flexible, scaffoldless ("virtual scaffold") manipulation of assembly and/or tissue shape in real time. Certain embodiments may remove the perturbing influence of a surface, core particle, or matrix, and rapidly concentrate cells to promote cell-cell interactions. Such embodiments may not require specific media or temperature control and/or processing before usage, and such may be compatible with standard culturing and diagnostic techniques.

Cells may be cultured, according to embodiments of the disclosure, with multiple cell types. Cells may be brought into proximity in a controlled manner to facilitate cell signaling and other cell-to-cell interactions, which may be physical or chemical, which may affect the properties or behaviors of the cells. One example of this would be a co-culture confrontation assay with in situ monitoring. Magnetic levitation may not require specific media, engineered scaffolds, molded gels, and/or bio-reactors. Embodiments of the disclosure may provide simple, flexible, and effective methods which may be suitable for a range of applications in biotechnology, drug discovery, stem cell research, or regenerative medicine.

Magnetic levitation, according to embodiments of the disclosure, may provide methods for 3D cell culturing with great potential for research and application. It may have significant advantages over traditional 2D growth methods and currently available 3D culturing methodologies. Relative to 2D culturing, cells may grow more rapidly without the need for cell passages, which is important for growing sensitive cells where time is a critical obstacle. In contrast to established 3D growth methods, magnetic levitation may not require specific media, or the fabrication of specially designed materials, engineered scaffolds, molded gels, and/ or bio-reactors. It also may offer spatial and temporal control of assembly shape, more rapid and controllable onset of cell-cell interactions, easier integration with imaging diagnostics, improved growth speed, and scalability.

Embodiments of the disclosure may address existing challenges for development of many cell-based applications. Some embodiments may provide novel methods for tissue assays. Some embodiments may prove valuable in high-throughput drug discovery due to the fast growth rate, available level of control, enhancement of cell-cell interactions, and compatibility with imaging techniques. The methods according to some embodiments may avoid surface contact with the cells. Such methods may hold promise for use in stem cell research, because the contact with polymeric or glass surfaces, often used in 2D cell culturing, may alter the biology of stem cells. The ability to spatially and temporally pattern multicellular assemblies may provide benefits for tissue engineering. From a practical standpoint, techniques according to some embodiments may be fast, easy, inexpensive, and require very little modification from standard cell culturing procedures.

Au-MIO-phage material may be patterned without or before introducing cells, according to some embodiments of the disclosure. Patterning of phage hydrogel may be useful, inter alia, because the phage may have many properties, such as a the ability to serve as scaffold for cell-growth, storage for cell nutrients, and vector for nanoparticle, DNA, or RNA delivery that can be cell-specific.

Figure 1:
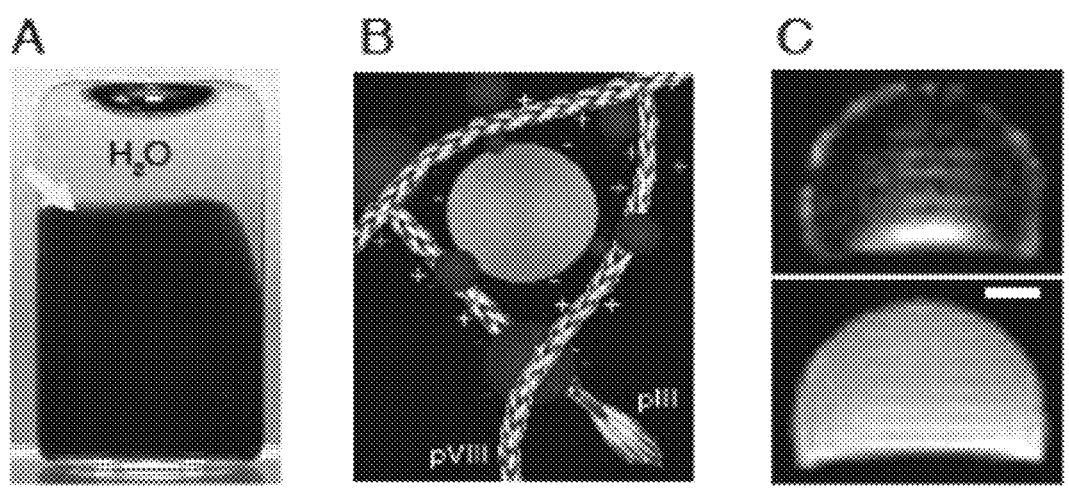

For certain embodiments of the disclosure involving cells, the cells may contain magnetic nanoparticles, have magnetic nanoparticles affixed to them, or have magnetic nanoparticles embedded in the assembly of cells. Any method for disposing magnetic nanoparticles inside or on cells or within an assembly is within the scope of this disclosure. In certain embodiments, hydrogels may be used to attach, infuse, and entrain magnetic particles into and onto the cells and assemblies.[13] For example, hydrogels may be used to introduce magnetic nanoparticles into cells, and, as the cells grow over time, the magnetic nanoparticles may be expelled from the cells and entrapped in the extracellular matrix of the assembly. Suitable hydrogels may be composed of nanoparticles, such as gold (Au) and/or magnetic iron oxide (MIO, magnetite, Fe3O4), with bacteriophage (Au-MIO-phage). Suitable hydrogels should contain at least one magnetic nanoparticle, whether it is superparamagnetic, paramagnetic, ferromagnetic, and/or ferrimagnetic. An example embodiment is illustrated in FIG. 1. Additionally, other embodiments of the disclosure provide other methods for making magnetic nanoparticles enter into cells, attach onto cells, or incorporate into an assembly of cells. Other ways known in the art include magnetic beads coated with a cell-targeting entity (e.g., a cell or protein specific receptor), or liposomes containing magnetic nanoparticles, and magnetic fields applied to construct and deliver cell sheets in vitro.[14-17] Different methods may have different advantages, and a person of ordinary skill in the art with the benefit of this disclosure will know which method(s) is more advantageous. For example, liposomes may be capable of delivering large quantities of nanoparticles. Hydrogels and coated magnetic beads may be designed to target specific cells. For example, hydrogels made of bacteria phage and one or more kinds of nanoparticles may serve as a scaffold for cell growth, storage for cell nutrients, or vector for nanoparticle, DNA, or RNA delivery that can be cell-specific. Hydrogels made of bacteria phage and one or more kinds of nanoparticles may have the ability to attach nanoparticles onto cells and infuse nanoparticles into cells, which may be of great value to allow modification and control of cells on the chemical and mechanical level.[13]

The phage (also referred to as bacteriophage) useful in the systems and methods of the present disclosure refers to any one of a number of viruses capable of infecting bacteria. Generally, a bacteriophage comprises an outer protein hull and an inner space comprising genetic material, which can be DNA or RNA. In certain embodiments, the phage may be a filamentous phage, such as, but not limited to, fd, f1, or M13 bacteriophage. In certain embodiments, the phage is a fd bacteriophage. Examples of suitable phage, as well as compositions comprising phage and nanoparticles and methods of forming such compositions, are described in International Patent Application Publication No. WO2006/060171,[13] the entire disclosure of which is hereby incorporated by reference.

In certain embodiments, the systems of the present disclosure may further comprise a targeting moiety, such as, but not limited to, a peptide or protein displayed on the bacteriophage or operatively coupled to the bacteriophage. The targeting moiety may be operably coupled (which includes being displayed on the surface of a bacteriophage) to a bacteriophage, a conductive assembly, or a bacteriophage assembly. In certain embodiments, the targeting moiety may be a peptide, and in specific embodiments, the peptide may be a cyclic peptide. Such cyclic peptides include, but are not limited to, cyclic peptides of the form CX7C, wherein C is cysteine and X is a random amino acid. In certain embodiments, larger protein domains such as antibodies or single-chain antibodies can also be displayed on or operatively coupled to the phage, i.e., a targeting moiety[69]. The assembly may also comprise a targeting moiety operably coupled, in particular covalently coupled, to a component of the system, e.g., phage or nanoparticle. In certain embodiments, the targeting moiety is a peptide. Suitable targeting peptide targeting moieties are described in International Patent Application Publication No. WO2006/060171[13], the relevant disclosure of which is incorporated by reference. In certain embodiments the targeting moiety is comprised in a pHI or pVIII protein of the bacteriophage. In certain embodiments, targeting moieties may be identified by screening peptides presented or included in the pIII and/or pVIII protein, in preferred embodiments the pVIII protein.

The systems of the present disclosure may further comprise an organizing agent that promotes organized packing of conductive nanoparticles. An organizing agent may include, but is not limited to, a peptide, a pyrrole, an imidazole, histidine, cysteine, or tryptophan. Furthermore, the systems of the present disclosure may comprise a therapeutic agent, such as a therapeutic molecule or nucleic acid. In certain embodiments, an organizing agent may induce aggregation, or couple two or more particles to form assemblies and is not limited to agents that induce an orderly arrangement of molecules, such as a lattice. In certain embodiments, the therapeutic agent is an organizing agent. In certain embodiments, the systems of the present disclosure may be comprised in a pharmaceutically acceptable composition. Certain embodiments of the disclosure include systems which further comprise a cell comprising or operatively coupled to the bacteriophage.

In some embodiments, an Au-MIO-phage may be assembled from Au, magnetite magnetic nanoparticles, and phage using a bottom-up, self-assembly method.[39, 40] The color and microstructure may be seen with darkfield microscopy, and may be qualitatively similar to previously reported observations of Au-phage assemblies (lacking MIO).[40] Generally, the Au-MIO-phage system may emulate the behavior Au-phage hydrogels, which may be predominantly stabilized by electrostatic interactions,[39, 40] as illustrated in FIG. 1. Both the Au and MIO particles may acquire negative charge under the aqueous solution conditions (pH 6.0)[39-41] and may be attracted to the positively charged phage. The phage and MIO may not form a hydrogel without Au, however, suggesting that the MIO may be less effective at establishing cross-linking between the phage. In some instances, the slightly smaller size of the MIO particles or the polydisperse size distribution may reduce the effectiveness at establishing a cross-linking MIO nanoparticles may be a common magnetic resonance imaging (MRI) contrast enhancer,[25] as illustrated in FIG. 1, the T2*-weighted MR images of Au-MIO-phage and a control Au-phage hydrogel (MRI).

The nanoparticles useful in the systems and methods of the present disclosure typically comprise one or more metallic conductive nanoparticles. Frequently, the metallic conductive nanoparticles will be capable of being magnetized, or magnetic. In certain embodiments, the metallic conductive nanoparticle comprises Au, Ag, Pt, Ti, Al, Si, Ge, Cu, Cr, W, Fe, or a corresponding oxide. In particular embodiments, the conductive nanoparticle is an Au cluster, such as, but not limited to, an Au-magnetite cluster. In certain embodiments, the conductive nanoparticles may be from about 2 nm to about 100 µm in diameter. In certain embodiments, multiple nanoparticles may be embedded in other materials that may be conductive or non conductive. In certain embodiments, the nanoparticles may be coated with conductive or non conductive materials. An example of the systems of the present disclosure containing Au-magnetite cluster nanoparticles is shown in FIG. 1.

In some embodiments, magnetic nanoparticles generally may be of any type of magnetic material. For example, suitable magnetic nanoparticles may be made of magnetite. In certain embodiments, the magnetite magnetic nanoparticles may have sizes below 30 nm, since magnetite particles may be superparamagnetic in that size range. In other embodiments, the magnetite magnetic nanoparticles may have larger sizes and may display remnant magnetization characteristic of bulk ferrimagnetism. Suitable magnetic nanoparticles may be of polydisperse particle size <50 nm, and may be stabilized with a surfactant of PVP (poly vinyl pyrrolidone). Such suitable magnetic nanoparticles may be commercially available from Sigma-Aldrich. A partial list of examples of other options for suitable magnetic nanoparticles include pure iron, nickel, cobalt, CoFe2O4, and NdFeB. Suitable magnetic nanoparticles may be coated or uncoated. One of ordinary skill in the art with the benefit of this disclosure will know which material and coating option is best for any given particular situation.

Magnetic nanoparticles have been used extensively in biological applications such as for MRI imaging,[25] cell sorting,[25] surface patterning,[26-30] mechano-conditioning of cells,[28] and studies of mechano-sensitive membrane properties.[28] Magnetite is a common choice of magnetic nanoparticle, since magnetite nanoparticles with sizes below 30 nm may be superparamagnetic, and larger sized magnetite nanoparticles may display remnant magnetization characteristic of bulk ferrimagnetism. In both cases, particles may be attracted to the maximum of an applied magnetic field.[31] Magnetic nanoparticles of many kinds may be modified to target specific proteins and have been shown to be biocompatible.[28] It is within the spirit of this disclosure to use magnetic nanoparticles of any type of material. A person of ordinary skill in the art with the benefit of this disclosure will know which type of material is best for a particular situation. For example, magnetite may be a good choice because it has a large saturation magnetization, so relatively large forces can be generated with relatively fewer particles. It is also easily obtained commercially and somewhat standard because much work has been done with it. Furthermore, magnetic nanoparticles may be coated or uncoated. A partial list of examples of other suitable options includes pure iron, nickel, cobalt, CoFe2O4, and NdFeB.

Microcarriers[34] or core particles,[35] which may contain magnetic material, have also been used to provide a surface for anchorage of dependent cells and allow the benefits of suspension culturing. Microcarriers, also referred to as core particles, beads, cell culture beads, microbeads, or micro-microcarriers, are solid particles, typically larger than nano-size, that may support the anchoring and growth of living cells.[34, 35] In some implementations, the microcarriers are larger than the cells. The magnetized particles are preferably coated with a cellular adhesive material, such as collagen, to facilitate cellular adherence.[35] Cells typically proliferate for some time before the cell-cell interfaces are larger than the cell-bead interfaces. Also, the beads which remain in the assembly may influence the mechanical properties of the tissue, which is important for tissue engineering applications. It may also be difficult to pattern small structures or small numbers of cells with microcarrier beads, because the beads are too large.

FIG. 1 illustrates an example Au-MIO-phage hydrogel used to deliver nanoparticles into and onto cells and within assemblies in certain embodiments of the disclosure. FIG. 1A illustrates an exemplary vial of a MIO-containing hydrogel (indicated by arrow) in water. FIG. 1B illustrates an exemplary scheme of electrostatic interaction of nanoparticles (spheres) with phage (elongated structures). Yellow (gold) and brown (MIO) nanoparticles are depicted (not drawn to scale). FIG. 1C illustrates an exemplary MRI image (T2-weighted) of purified hydrogel in solution, MIO-containing hydrogel (top panel), average T2*=76 ms and MIO-free hydrogel control (bottom panel), average T2*=253 ms. The image contrast between the MIO-containing hydrogel and the negative control results from the reduction in T2*relaxation constant in the presence of MIO nanoparticles (scale bar=2 mm).

Figure 2:
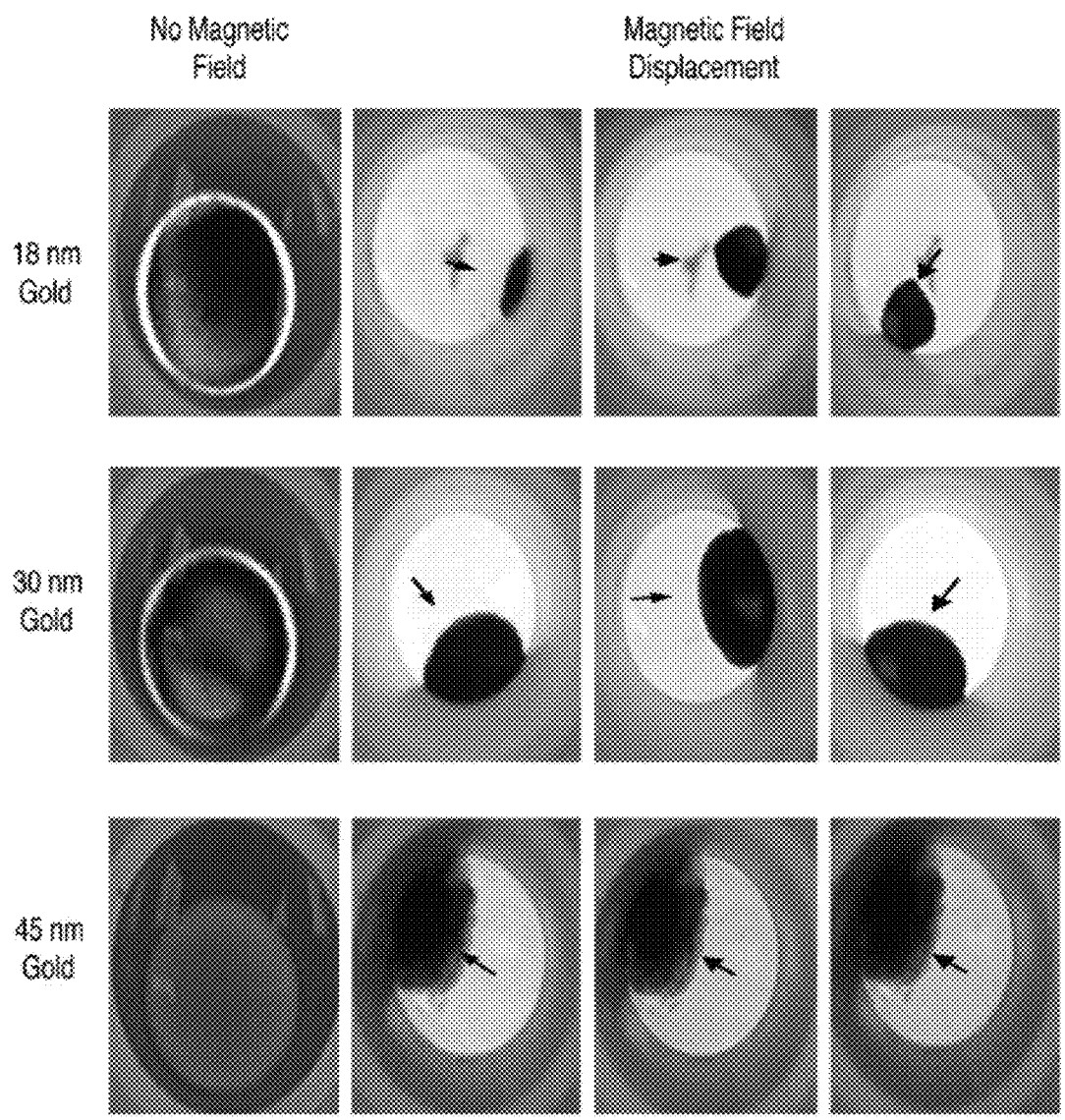

According to some embodiments, magnetic fields, created either with permanent magnets or current-carrying wires, may apply forces to the magnetic nanoparticles, and thus to the cells and/or assemblies. Such forces may move the cells and/or assemblies towards, or hold them in the region of, maximum magnetic field amplitude. Due to the flexibility of shaping and changing magnetic fields, the shape of cells and the resulting tissue samples they form may be shaped and changed, as is illustrated in FIG. 2. A person of ordinary skill in the art with the benefit of this disclosure will know whether it is more advantageous to use permanent magnets, current carrying magnets, or some combination. For example, permanent magnets may produce larger fields and forces and collect more cells. Wires may be more easily patterned to form magnetic field patterns, may make smaller structures, and may be more flexible for manipulation.

FIG. 2 illustrates magnetic displacement of Au-MIO-phage, according to some embodiments of the disclosure. In this illustration, the Au-MIO-phage may be prepared with different sizes of Au nanoparticles (18 nm, top panel; 30 nm, middle; and 45 nm, bottom) under the same concentration of phage and MiO nanoparticle. Here, the hydrogel specifically used is Au-MIO AAVP-RGD-4C (AAVP, adeno-virus associated virus phage),[38] but the particular kind of phage is not critical to the success of the invention. The hydrogels prepared with the different sizes may show different response to the magnetic field, but, in general, they may be all attracted where the magnetic field is strongest. For this data, the permanent magnet may be placed just outside the well, as indicated by arrow pointing towards magnet.

Figure 3:
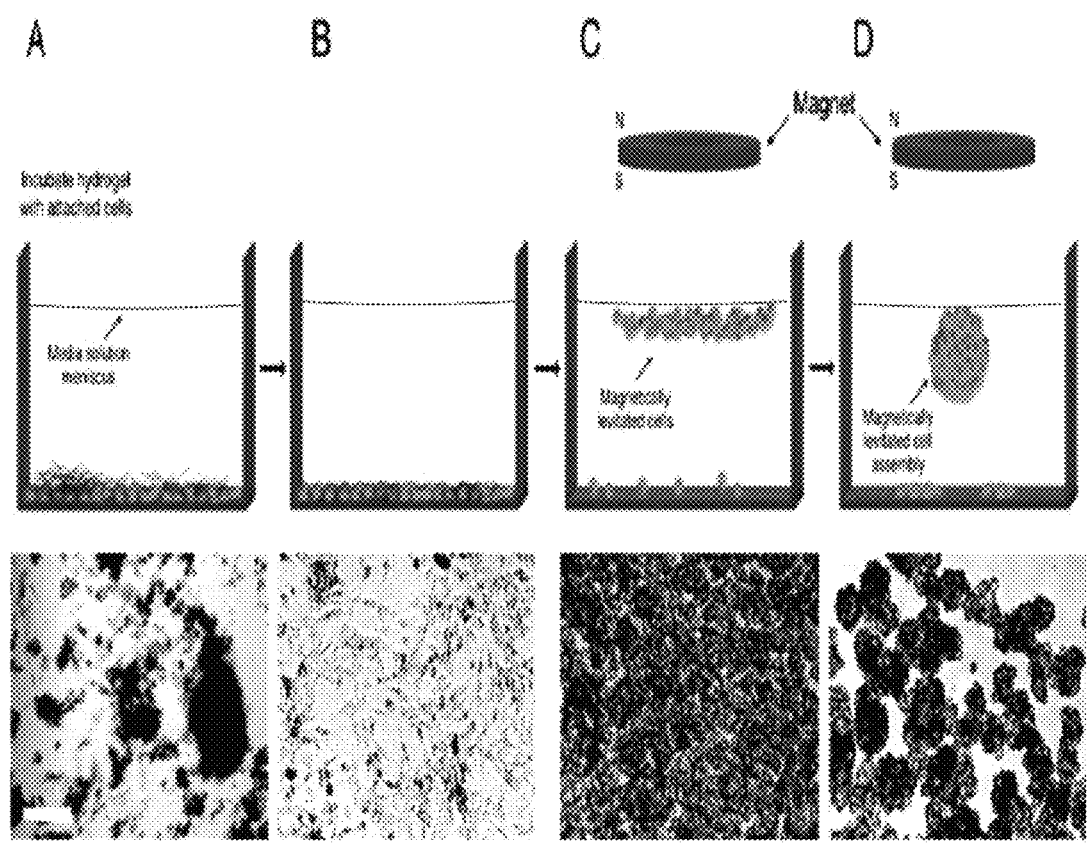

In some embodiments, cells may be magnetically levitated. As illustrated in FIG. 3, cells may be grown in three-dimensions away from a surface, sometimes referred to as levitated cell culturing. For example, murine C17.2 neural stem cells (NSC) may be so cultured.25 The cells may be grown at the liquid-air interface. Neural stem cells may be attached to the flat bottom surface of the culture plate, and a preparation of MIO-containing hydrogel may be dispersed through pipetting. Often, size distribution of hydrogel fragments may not be critical. As illustrated in FIG. 3A, the admixture may be incubated under standard tissue culture conditions. Overnight incubation may provide results similar to previous studies using confocal microscopy to show that targeted phage particles and gold nanoparticles adhere to outer mammalian cell membranes and undergo receptor-mediated internalization.[39, 40] As illustrated in FIG. 3B, neural stem cells may be rinsed with phosphate-buffered saline (PBS), and hydrogel remnants may be removed. The neural stem cells may be detached from the surface with a standard trypsin:EDTA treatment.[39, 40] A magnet may placed above the tissue culture dish, as illustrated in FIG. 3C. The admixture of neural stem cells and MIO-containing hydrogel may co-rise to the air-liquid interface due to the attraction of nanoparticles to regions of high magnetic field.[31] In some embodiments, the magnetic field may concentrate assemblies of levitated cells together (nearby, in close proximity, and/or in physical contact), allowing cell-cell interactions, for example cell signaling through chemical or mechanical pathways. Cells may not be able to leave the liquid due to surface tension. As illustrated in FIG. 3D, there may be evidence of large- and small-scale 3D multicellular assembly features with characteristic and reproducible branching morphogenesis.[42, 43]

In certain embodiments of the disclosure, cells may be magnetically levitated away from a surface, which may enable the culturing of 3D assemblies, including creation and manipulation of levitated patterns and shapes of assemblies. In some embodiments, the shape of an assembly may be influenced to form a particular 2D or 3D pattern or distribution. When more than one cell type is present, influencing the shape of a assembly may also include changing the relative arrangement of different populations of cells within the assembly. For example, layers of different types of cells may be formed. The layers may be formed as sheets, or the layers may vary radially, as when one type of cell is grown around a central assembly of another type of cell. Illustrations of such an embodiment are shown in FIGS. 3-13.

The magnetic fields utilized in systems and methods of the present disclosure may be provided by any suitable source. Such sources include, but are not limited to, magnetic fields generated by magnets, magnetic fields generated by the flow of electric current, or a combination thereof. In certain embodiments, suitable magnetic fields generated by the flow of electric current may be provided by the flow of electric current through one or more conductive wires. Some embodiments specifically utilize ring magnets. Magnetic nanoparticles may be preferentially drawn to the axis of symmetry of a ring magnet, while light may be allowed to pass through the central opening of a ring magnet. These two effects, taken together, may allow better visualization of assemblies and cell culturing when cells are levitated with ring magnets. Ring magnets are traditionally permanent, circular magnets, though any type of magnet of any geometry affording a central opening would be within the spirit of the disclosure. An example ring magnet is illustrated in FIGS. 3C & D.

Extremely large magnetic fields (>4 T), such as in the bores of superconducting MRI magnets, have been used to levitate cells through the natural diamagnetism of biological material,[32] and smaller magnets can be used to trap cells immersed in a media with a high concentration of paramagnetic salts.[33]

Other schemes for controlling the 3D shape of assemblies may require the fabrication of specially designed materials, engineered scaffolds,[36] molded gels, and/or bio-reactors based on rotation or agitation. Often, such materials and instruments may be costly, cell specific, and not biocompatible, which limits their applicability. Biodegradable porous scaffolds and protein matrices that promote cell adhesion and mimic or promote formation of extracellular matrix are routinely used for producing 3D ex vivo tissue samples,[37] but they may suffer from slow propagation of cells into the constructs and establishment of cell-cell interactions,[14-17] and challenges in designing a biocompatible scaffold that does not perturb cell properties.[7, 11]

Embodiments of the present disclosure may provide 3D cell growth with flexible, scaffoldless ("virtual scaffold") manipulation of tissue shape in real time. Certain embodiments remove the perturbing influence of a surface, core particle, or matrix, and rapidly concentrate cells to promote cell-cell interactions. Such embodiments may not require specific media or temperature control and/or processing before usage, and may be compatible with standard culturing and diagnostic techniques.

FIG. 3 illustrates a levitated cell assembly, according to some embodiments of the disclosure. The upper panel of each frame illustrates a schematic, and the corresponding lower panel may be a representative microphotograph of neural stem cells (NSC) at the same stage of the process. FIG. 3A illustrates an Au-MIO-phage hydrogel dispersed over cells, wherein the mixture may be incubated to deliver nanoparticles onto and into cells. The dark blotches illustrate macroscopic fragments of hydrogel. FIG. 3B illustrates excess, non-interacting hydrogel fragments which may be removed during washes. FIG. 3C illustrates the magnetized admixture rising to the air-medium interface when the magnet is placed. This image illustrates the admixture after 15 min of levitation. FIG. 3D illustrates characteristic and reproducible multicellular structures formed after 12 h of levitation. Darker regions may result from increasing optical thickness of the cell mass. The scale bars in each Figure are 30 mm.

Figure 4:
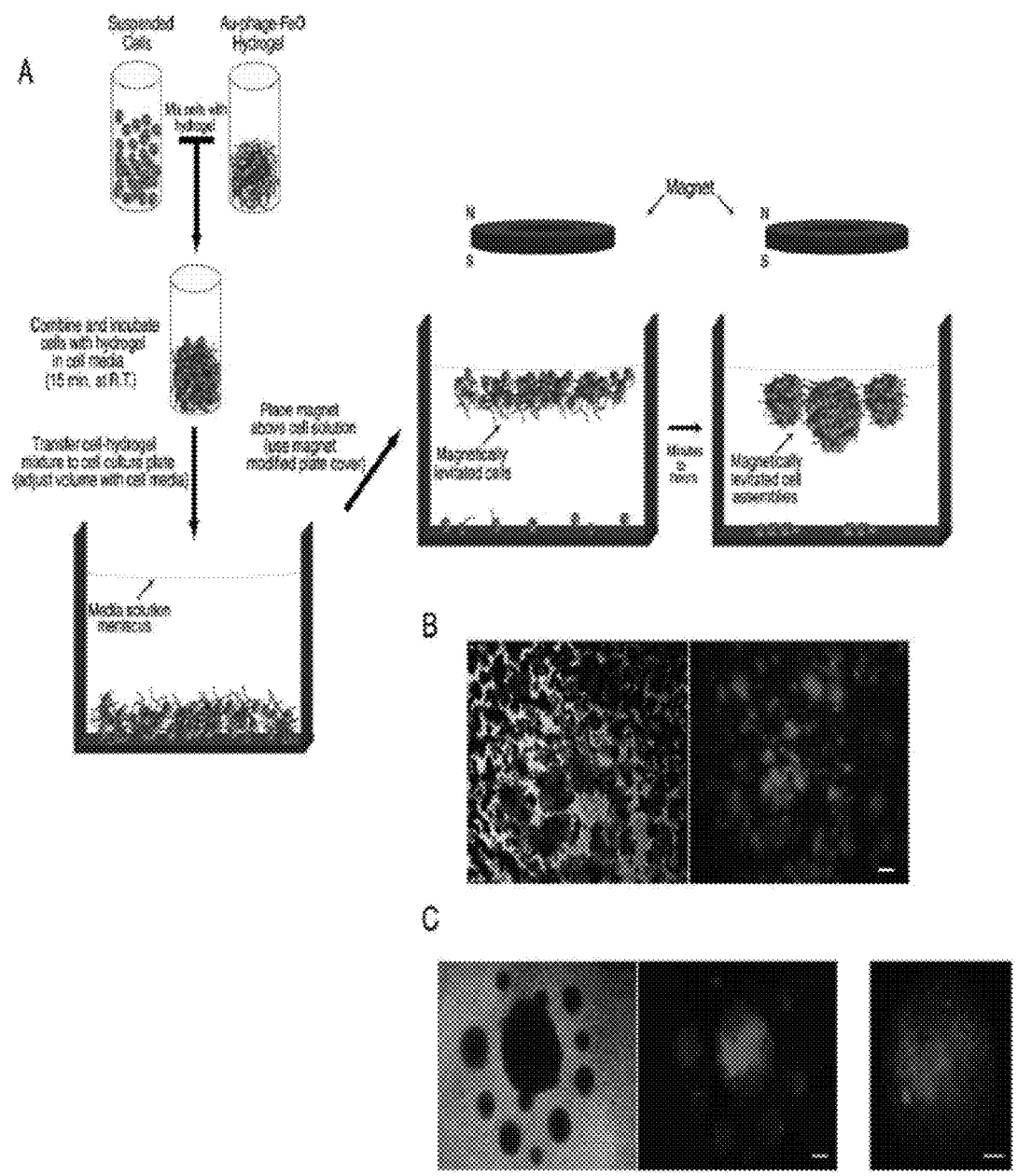

FIG. 4 illustrates magnetic levitation of a cell in the absence of cell attachment, according to certain embodiments of the disclosure. FIG. 4A illustrates an Au-MIO-phage incubated with suspended cells for 15 min. After incubation, the Au-MIO-phage plus cell admixture may be transferred to a cell culture dish. A magnet may be added to levitate the magnetized cells. FIG. 4B illustrates phase contrast (left) and fluorescence photomicrographs (right) of levitated mCherry-expressing normal human astrocytes 15 min after the onset of levitation and 48 h after the onset of levitation, wherein the scale bar is 200 µm. By 48 h, multicellular spheroids may be observed. The far right panel in FIG. 4C shows a magnified image of a spheroid (mCherry fluorescence, 50 µm scale bar).

Some embodiments provide a procedure for levitated culturing through magnetic levitation with no surface attachment. Suspended cells may be incubated with the Au-MIO-phage. The incubation may last for about 15 min, after which time the suspended cells may be magnetically levitated, as illustrated in FIG. 4. Without limiting the disclosure to a particular theory or mechanism of action, it is nevertheless currently believed that the yield of levitated vs. non-levitated cells is influenced by the amount of Au-MIO-phage, incubation time, strength and gradient of magnetic field, and distance from magnet to bottom surface. As illustrated in FIGS. 4B and C, mCherry-transfected normal human astrocytes may be cultured for 15 min and 48 h. Such procedures may provide a simpler and faster technique, although the yield of cells may be lower. Such procedure may obviate the need for surface attachment, so that it may be used with cell stocks directly thawed from frozen storage. This technique may be applied to a variety of cell types. For example, human glioblastoma cells (FIG. 5), differentiated neural stem cells (FIG. 6), human astrocytes (FIG. 7), glioblastoma assemblies (FIG. 8), and melanoma (FIG. 9).

Figure 5:
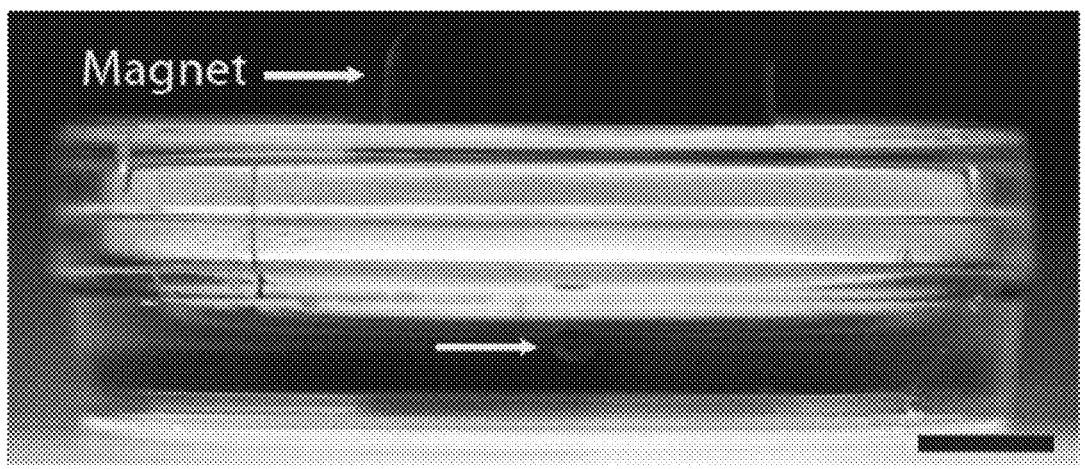
FIG. 5 illustrates a magnetically levitated assembly, according to some embodiments of the disclosure.

FIG. 5 illustrates a magnetically levitated cell assembly, according to some embodiments of the disclosure. Human glioblastoma cells (lower arrow) may be treated with magnetic iron oxide (MIO)-containing hydrogel and held at the air-medium interface by a magnetic field created by the magnet attached to the top of the tissue culture plate (upper arrow). This illustrates the scale bar is 5 mm and the image taken at 48 h of culturing.

Figure 6:
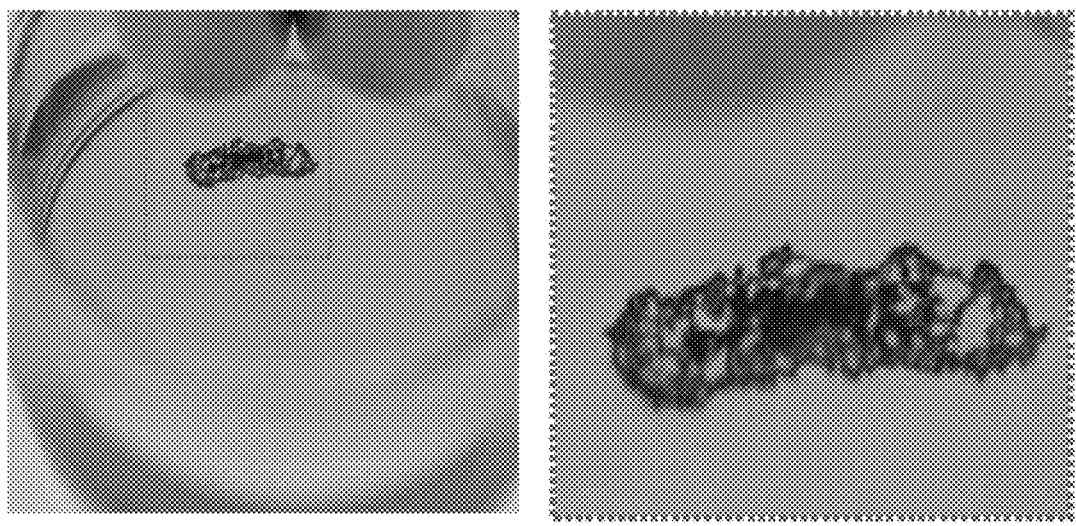
FIG. 6 illustrates magnetically levitated differentiated murine neural stem cells (NSC), according to embodiments of the disclosure.

FIG. 6 illustrates magnetically levitated differentiated murine neural stem cells (NSC), according to embodiments of the disclosure. Surface attached NSCs were treated with mitomycin (1 μg/ml for differentiation) for 8 h prior to suspending cells. This illustrates 24 h after onset of levitation.

FIG. 7 illustrates magnetically levitated human astrocytes, according to certain embodiments of the disclosure.

Figure 8:
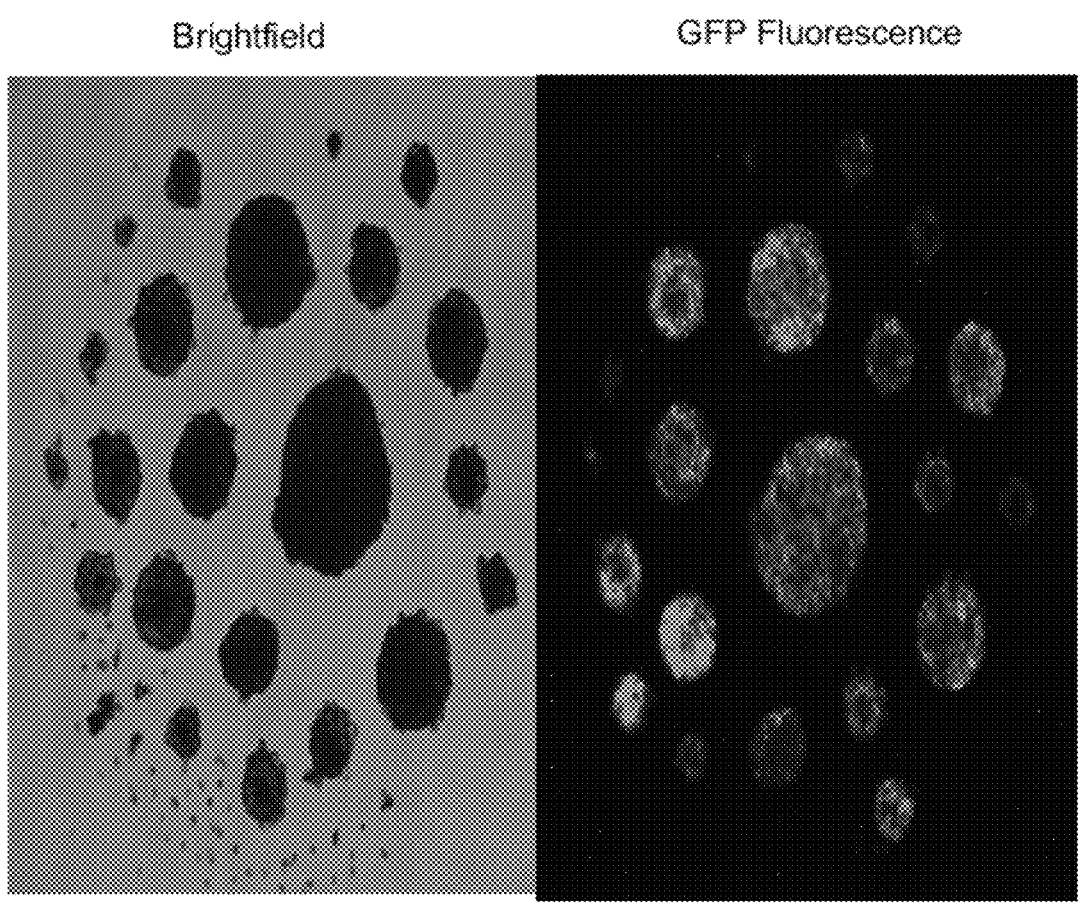
FIG. 8 illustrates magnetically levitated glioblastoma assemblies, according to certain embodiments of the disclosure.
Figure 9:
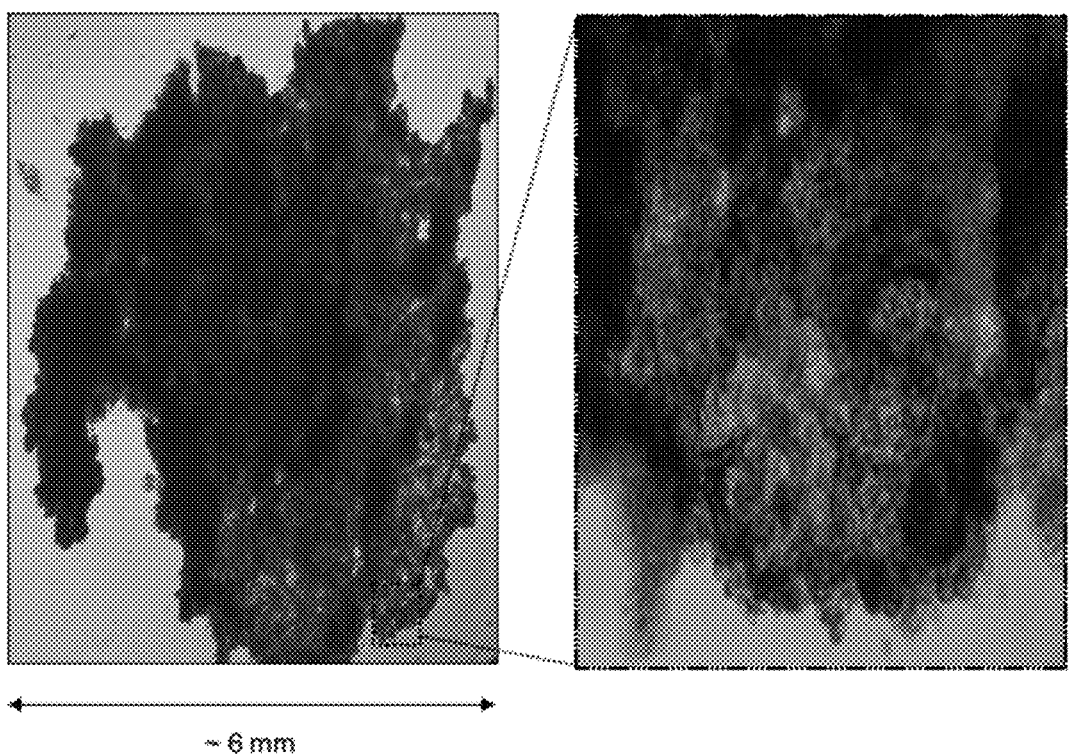
FIG. 9 illustrates magnetically levitated melanoma cells, according to certain embodiments of the disclosure.

FIG. 8 illustrates magnetically levitated glioblastoma assemblies, according to certain embodiments of the disclosure.

FIG. 9 illustrates magnetically suspended melanoma (B16) cells, according to certain embodiments of the disclosure, which may grow as a sheet. Melanoma, a rare but deadly type of skin cancer, is generally a malignant tumor which manifests from the uncontrolled growth of pigment cells, called melanocytes.

Figure 10:
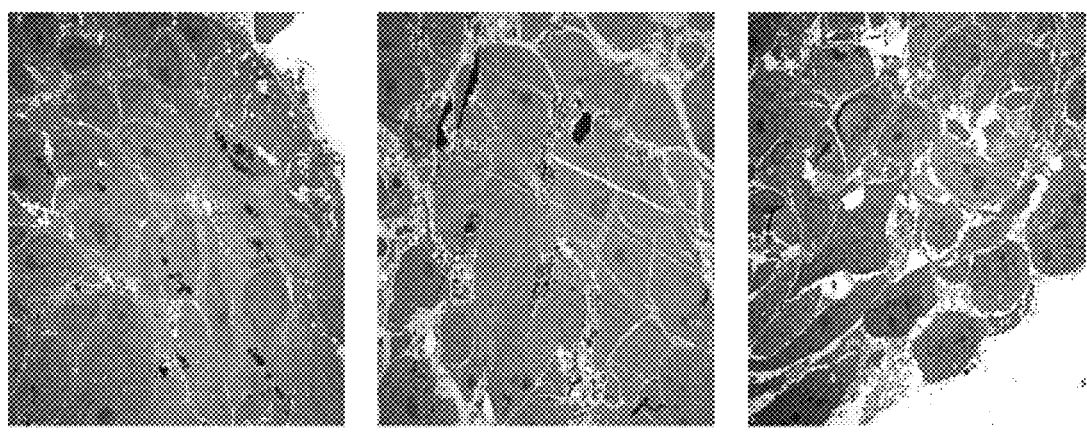
FIG. 10 illustrates transmission electron microscope (TEM) images of human glioblastoma cells grown with magnetic levitation, according to embodiments of the disclosure.

While mammalian cells may eventually process biological material such as phage,[38] the cellular fate of metal nanoparticles is not well understood. Some embodiments of the disclosure, however, may demonstrate the long-term presence of MIO nanoparticles in levitated assemblies. For example, after months of levitated culturing, viable multicellular assemblies may drop when the magnet field is removed, and may re-levitate when the magnet field is reapplied. The long-time dynamics of MIO nanoparticles in cells is not entirely understood.[44-46] However, as illustrated in FIG. 10, transmission electron microscope (TEM) analysis may show that, after about one week of levitated culturing, levitated human glioblastoma cells may predominantly release nanoparticles into the media and/or extracellular matrix. Without determining a molecular mechanism(s) for these observations (such as secretion, apoptotic cell death, or a combination), the apparent "entrainment" of metal nanoparticles in the assembly may explain the system's ability to levitate assemblies for relatively extended periods of time.

TEM of cross-sections of spheroids of human glioblastoma cells grown through magnetic levitation, according to one embodiment of the disclosure, show the location of nanoparticles at different stages, as illustrated in FIG. 10. For example, after 24 h of levitation, the bulk of nanoparticles may be contained in the cell cytoplasm, consistently with previous reports.[39, 47, 48] The cells may have processed the nanoparticles after 8 days of culturing, and they may appear in the extracellular matrix (ECM). It may be the case that cellular division and growth of the spheroid presumably leads to a differential distribution of the nanoparticles (preferentially present in the center of the spheroid rather than in the outer region).

FIG. 10 illustrates transmission electron microscope (TEM) images of human glioblastoma cells grown with magnetic levitation, according to embodiments of the disclosure. Towards the left of FIG. 10, nanoparticles (black) may be seen inside the cells after 24 h of culturing. In the middle of FIG. 10, nanoparticles may be seen in the central region of the tissue spheroid but largely in the extracellular matrix after 8 d of culturing. Towards the right of FIG. 10, the outer regions of the spheroid (after 8 days of culturing) may be seen to not contain detectable nanoparticles. In this illustration, the scale bar is 5 μm. Cohesiveness of the assembly and retention of nanoparticles in the assembly may allow the assembly to be levitated as described in text.

Figure 11:
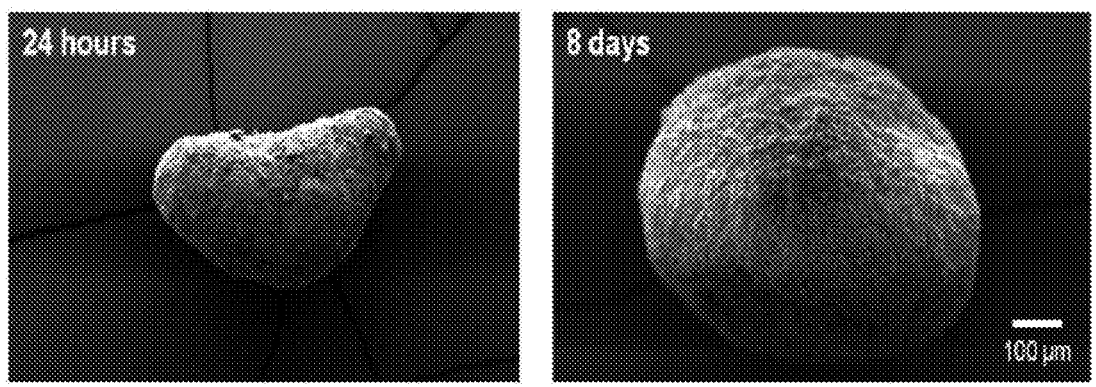
FIG. 11 illustrates a scanning electron microscope (SEM) images showing levitated culturing from 3D structures, according to embodiments of the disclosure.

In some embodiments, culturing by magnetic levitation may produce 3D assemblies. As illustrated in FIG. 11, scanning electron microscopy (SEM) images may show the 3D nature of human glioblastoma cells grown under magnetic levitation, according to embodiments of the disclosure. For example, SEM images may be captured with the JSM 5900 scanning electron microscope, commercially available from JEOL USA, Inc., of Peabody, Mass., equipped with backscatter electron detector and digital camera. Additionally, multicellular structures of human glioblastoma cells may be fixed, critical-point dried, and coated with Au/Pd.[49]

FIG. 11 illustrates a scanning electron microscope (SEM) images showing levitated culturing from 3D structures, according to embodiments of the disclosure. SEM of human glioblastoma cells grown under magnetic levitation for 24 h may be seen towards the left, while that for and 8 d may be seen towards the right, wherein the scale bar is 100 μm.

Some embodiments may provide results which compare favorably with traditional methods. For example, culturing by magnetic levitation may provide favorable results when compared with traditional 2D culturing. Cell growth may be assessed via visual and quantitative monitoring of the formation rate, size, and viability of genetically-modified human glioblastoma cells over a period of 8 d by monitoring the fluorescence from stable protein expression of mCherry, as illustrated in FIG. 12A. Cells may come together within 30 min of levitation. Moreover, a cohesive multicellular assembly may emerge by 24 h, and a spheroid shape may form between 3-8 d. Intense red fluorescence from mCherry protein expression may be observed, which may confirm cell viability within the 3D assembly. In some embodiments, the assemblies may be maintained for at least as long as 12 weeks or more. The growth rate of magnetically levitated cells compared to that of cells cultured in standard 2D culture plates is illustrated in FIG. 12B. In contrast to the indicated exponential trend for the growth of levitated cells, cells cultured in 2D show a linear growth pattern, a typical feature of surface attached assemblies.[50] In part because of the volume accessible during 3D growth of levitated cells, a large assembly may be attained without the de-attachment/re-plating cycles ("passage") generally required in standard 2D tissue culturing.

Cells cultured by magnetic levitation, according to embodiments of the disclosure, may show similarity to in vivo tissues. Such similarities may have advantages for certain applications. For example, protein expression in Human glioblastoma cells may exhibit similarities. FIG. 12C illustrates a comparison of the expression of the marker N-cadherin in levitated cells, cells grown on a 2D surface of a petri dish, and cells in tumor xenografts in immunodeficient mice. Without limiting the disclosure to a particular theory or mechanism of action, it is nevertheless currently believed that N-cadherin, a transmembrane protein that mediates cell-cell interactions through homotypic cell adhesion interactions,[51] may provide an expression pattern which actually recapitulate at least some in vivo-like traits of 3D-grown cells. Indeed, 2D assemblies may show N-cadherin scattered in the cytoplasm and nucleus but absent from the membrane while levitated cells express N-cadherin in the membrane, cytoplasm, and cell junctions (akin to the protein expression pattern observed in tumor xenografts). This observation is qualitatively consistent with results recently reported by Ofek et al.,[51] in which cartilage grown in vitro also yielded differential N-cadherin expression pattern in levitated, relative to 2D culturing. Absent levitation, there may be no detectable alteration in N-cadherin expression in attached glioblastoma cells with any combination of MIO-containing hydrogels and/or magnetic fields. Thus, in some embodiments, magnetically induced levitation of in vitro cells may provide a complementary cheaper surrogate than the labor- and cost-intensive generation and maintenance of human brain tumor xenografts in immunodeficient mice.[52] In general, indications are that magnetic levitation may produce cells that are more like cells in living organisms that obtained with traditional artificial culturing techniques.

Figure 12:
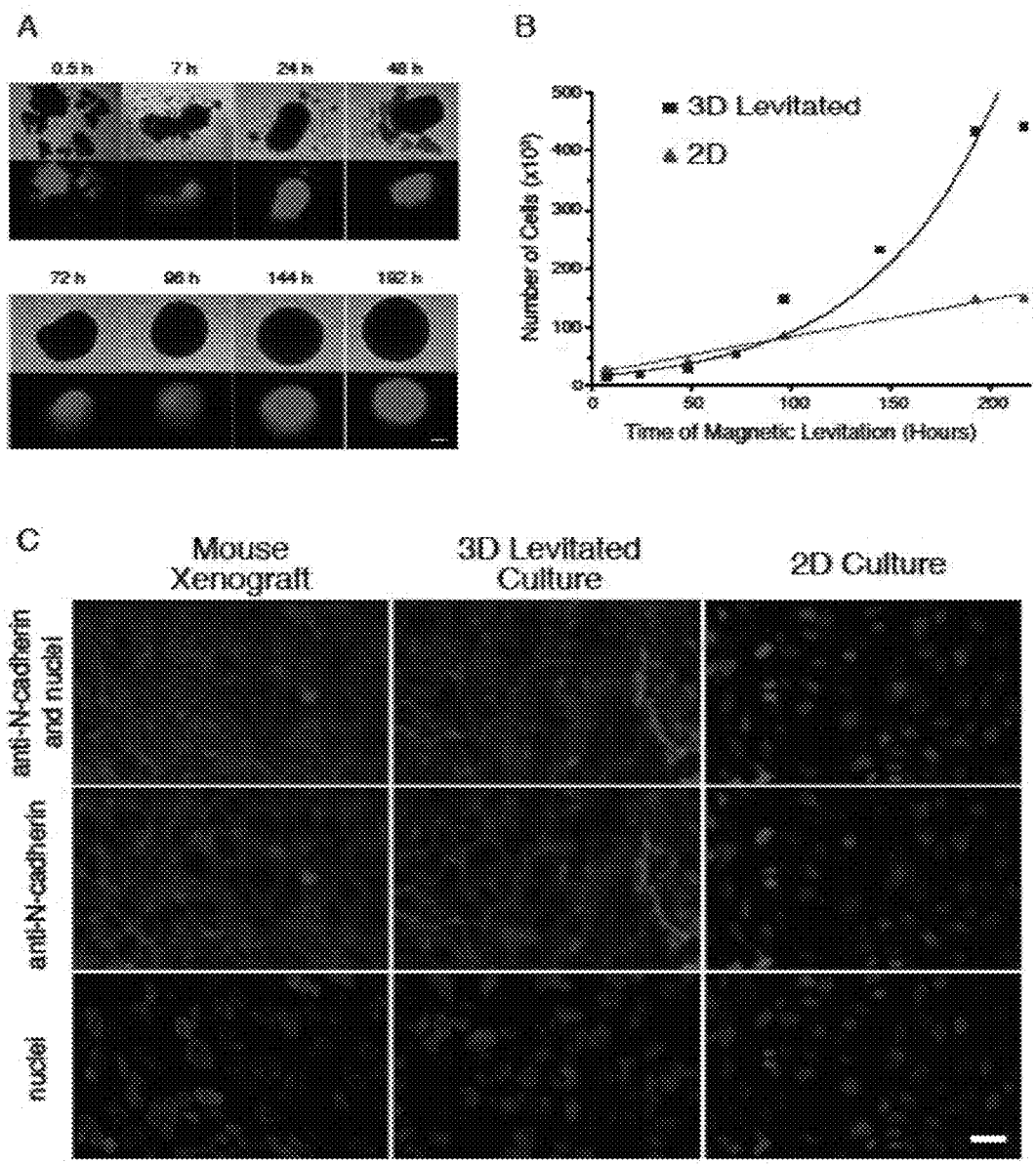

FIG. 12 illustrates a comparison of levitated cell assembly with 2D assembly and mouse xenograft, according to certain embodiments of the disclosure. FIG. 12A illustrates phase contrast (top) and fluorescence (bottom; mCherry-expressing cells through stable transfection) photomicrographs of levitated human glioblastoma cells which were monitored over an 8 d interval. Within a few hours, the cells may come together. By 24 h, there may be a defined multicellular assembly of human glioblastoma cells that eventually formed a spheroid. In this illustration, the scale bar is 200 μm. In FIG. 12B, the number of cells as a function of time for the levitated cell assembly in 12A are illustrated (squares, blue line indicates exponential growth trend). Also illustrated is a representative 2D assembly (triangles, red line shows linear trend). FIG. 12C illustrates immunofluorescence of N-cadherin (red, Alexafluor 555) and nuclear staining (blue, DAPI) of mouse brain containing human glioblastoma xenograft, human glioblastoma cells cultured by 3D magnetic levitation for 48 h, and human glioblastoma cell standard 2D assembly attached to a glass slide cover slip, wherein the scale bar is 10 μm.

Figure 13:
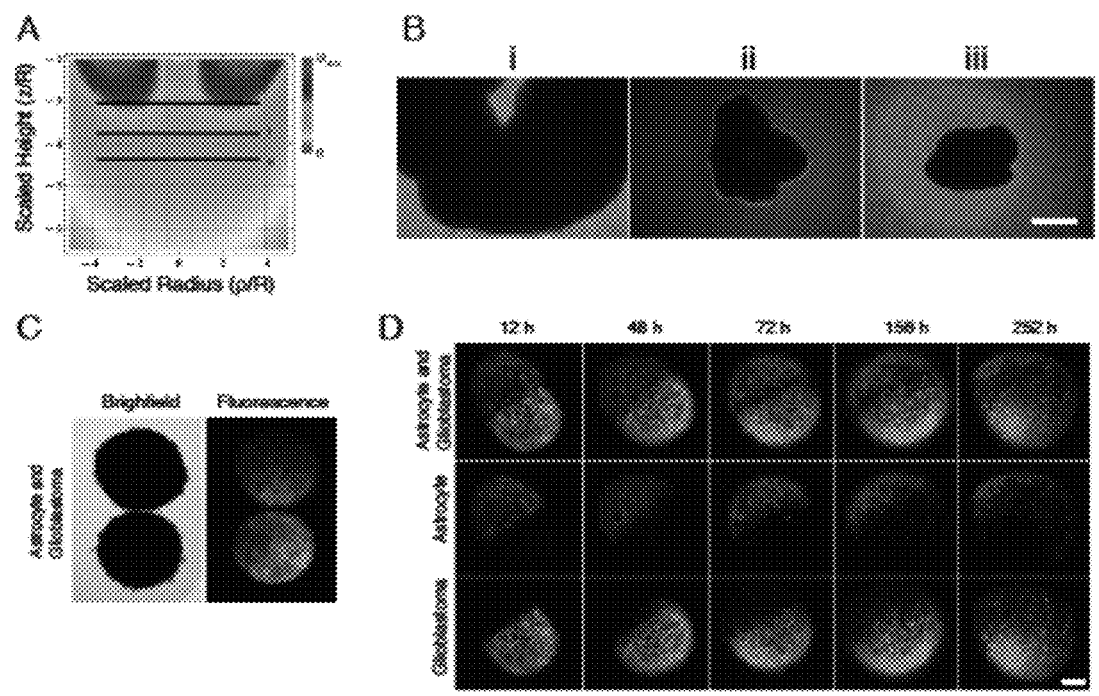

Methods according to certain embodiments of the disclosure may provide cell patterning, shape control, and time-dependent shape manipulation. As previously discussed, magnetic levitation may result from the attraction of the MIO nanoparticles to regions of high magnetic field. In some embodiments, the magnetic field may be shaped by appropriately shaped magnets or varied temporally with electromagnets or by moving permanent magnets. In such embodiments, there is great potential for spatially patterning cells and manipulating structures in time. The magnetic field may generally functions as an adjustable, invisible scaffold on which to mold magnetized multicellular assemblies, as illustrated in FIG. 13. Thereby, complex cell shapes on all length scales may be realized, for example, through the use of electromagnets and microfabrication techniques.

Multicellular glioblastoma assembly structures with ring-shaped permanent magnets of different diameters and varying magnetic force strengths may be levitated, as illustrated in FIG. 13. The resulting structures may directly reflect the properties of the magnetic field used. The largest and strongest magnet may generate the largest structure, as illustrated in FIG. 13B. Furthermore, because the field pattern at the meniscus may have a local minimum on axis (under the imaging hole), cells may grow in a ring pattern that traces the maximum of the field. For small magnets, also illustrated in FIG. 13B, with smaller holes, the on-axis field minimum may become insignificant or vanish at the height of the cells. This may ultimately yield a compact multicellular assembly, rather than a ring-shaped one.

Magnetic levitation, according to embodiments of the disclosure, may provide precise temporal and/or spatial control of the pattern of cells. Bringing cells into proximity may facilitate interactions between populations of cells that were originally distinct. This may be done in an environment conducive to visualization or molecular imaging in situ. For example, such system attributes are illustrated (i) with single-cell types in FIGS. 3-9 and (ii) with different cell types (or populations) in confrontation assays in FIGS. 13C-D between co-cultured human glioblastoma cells (GFP-transfected; green cells) and normal human astrocytes (mCherry-transfected; red cells). Assemblies that were originally cultured separately may be magnetically confronted, as illustrated in FIG. 13 C (deemed time zero), and their interaction may be monitored for 14 d, as illustrated in FIG. 13D). Although a clear interface separating the cell structures may be initially evident, by 12 h, the populations may begin to fuse and lose their individual spherical shapes. After 3 d, the confrontation assay may coalesce into a single spheroid with the human glioblastoma cells invading the structure composed of normal human astrocytes. These embodiments may have practical application in relation to glioblastoma multiforme, the most common, invasive, and lethal type of astrocytic brain tumor.[53-57] Normal human astrocytes are generally among the main cell type forming the brain and spinal cord and are known to support the malignant glioma invasion into brain tissue in vivo.[58] Levitated culturing may be used for analysis of brain tumor invasiveness of normal brain cells in confrontation culture assays, which have long been correlated with clinical results[58].

In some embodiments, more than two cell types and/or populations of cells may be co-cultured. Levitated cells may be cultured in the presence of a feeding layer. The force being applied to cells and receptors may be varied by changing the magnetic field, for example, by using electromagnets or by moving permanent magnets. These methods may have practical application in research on mechanosensitive mechanisms in cells, such as in stem cell research.

In conjunction with FIG. 12, which illustrates levitated cells showing striking resemblance to tissue in living organisms, FIG. 13 illustrates the potential for magnetic levitation, according to some embodiments, to form the basis for drug efficacy and drug screening assays. Various compounds may be introduced to see if any of them slow the invasion of the cancer. Positive results may indicate promising cancer-fighting drugs. The results may be indicative of drug efficacy on tumors in living organisms, due to the fact that the levitated cells resemble living tissues.

FIG. 13 illustrates a control of shape and position of cells during cell culturing; co-culturing, and confrontation assay, also known as invasion assay, according to embodiments of the disclosure. FIG. 13A illustrates calculated magnetic field patterns of ring magnets used for 3-D cell assembly in 13B. Height and radius were scaled by the inner radius of the magnet (R). Magnets in 13B i, ii, and iii have R values of 2.8, 2.3, and 1.7 mm respectively. For each magnet, the outer radius is about 4R and the thickness is about equal to R. A universal plot gives an approximation of the field profile as a function of normalized coordinates. The color scale is linear and Bmax ~3000, 2000, and 1500 G for frames B i, ii, and iii. The center of the magnet is taken as z=0. The black lines indicate heights of the cell assemblies in frames B i, ii, and iii. Magnetized hydrogel and cells may be attracted to regions of maximum field but cannot leave the medium due to surface tension. FIG. 13B illustrates resulting human glioblastoma spheroids assembled from magnetic fields described in FIG. 13A. For the largest radius magnet (i), at the height of the assembly the field is peaked away from the symmetry axis, leading to a ring-shaped cell pattern. The cells display this spatial distribution immediately at the onset levitation, wherein the scale bar is 400 μm. These 3D multicellular structures were cultured in tissue culture plates with covers modified by attaching a ring-shaped magnet above each well. FIG. 13C illustrates brightfield and fluorescence photomicrograph of human glioblastoma cells (green; GFP-expressing cells) and normal human astrocytes (red; mCherry-labeled) cultured separately and then magnetically guided together (time=0). FIG. 13D illustrates confrontation between human glioblastoma cells and normal astrocytes in FIG. 13C, monitored for 10.5 d. Invasion of the spheroid composed of normal human astrocytes by human glioblastoma cells of serves as a standard assay of malignant glioma invasiveness.34 In this figure, the scale bar is 200 μm.

Another embodiment of the disclosure may provide cell printing or patterning on a surface. For example, this may be done by magnetically guiding an assembly of cells to a surface, allowing some cells to attach to the surface, and moving the ball of cells over the surface to form a pattern of cells, as illustrated in FIGS. 14 and 15. Alternatively, it may be accomplished by using either current carrying wires or permanent magnets, which may create a field profile in the desired shape for the cells, thereby allowing initially free cells to move in the field to affix in the desired pattern, as illustrated in FIGS. 16-20.

In some embodiments, cells may be patterned on a surface through printing techniques. Printing cells on a surface may be beneficial for a wide range of medical applications, such as tissue/organ replacement and wound healing.[60-68] FIGS. 14 and 15 demonstrate the potential of certain embodiments of this disclosure for cell printing/graphing. In some embodiments, this procedure can be achieved after treating cells with Au-MIO-phage. Therein, the cells may be levitated for a desired period of time, which may vary from minutes to days, and the cells may be magnetically guided to the surface for patterning. In some embodiments, after cells start to attach to surface, the cells may then displace the 3D structure to a new position where surface-attached cells will remain attached. In some embodiments, the cells may be magnetically guided cells directly to printing magnetic pattern, bypassing cell levitation. With any of these procedures, the cells may attach to surface and remain viable. These procedures may produce a pattern of cells on the surface. For example, FIG. 15 illustrates a letter N written on a surface in this way.

FIG. 14 illustrates an example of cell patterning on a surface using a cell printing technique, according to some embodiments of the disclosure. An assembly that was initially levitated was guided to a plastic surface. After 12 hours, some cells had migrated out of assembly and attached to plastic.

Certain embodiments may combine lithographically patterning with permanent magnets. For example, when using small magnetic field patterns, a uniform background field may be applied with a large permanent magnet or electromagnetic. The surface may be oriented in any direction with respect to gravity and does not have to be flat. This may increase the magnetization of the magnetic particles and increase the forces on the nanoparticles, cells, and materials.

FIG. 15 illustrates an example of cell patterning on a surface using a cell printing technique, according to one embodiment of the disclosure. Fluorescence image of magnetically patterned GFP expressing HGBM using cell printing technique. Towards the left, it can be seen that the letter N was generated on tissue culture plastic by magnetically guiding Au-phage-MIO treated HGBM cells to specific points at the surface of a tissue culture plate. Towards the right, a photomicrograph of HGBM cells can be seen attached to the tip of the N pattern (indicted by dotted lines).

Figure 20:
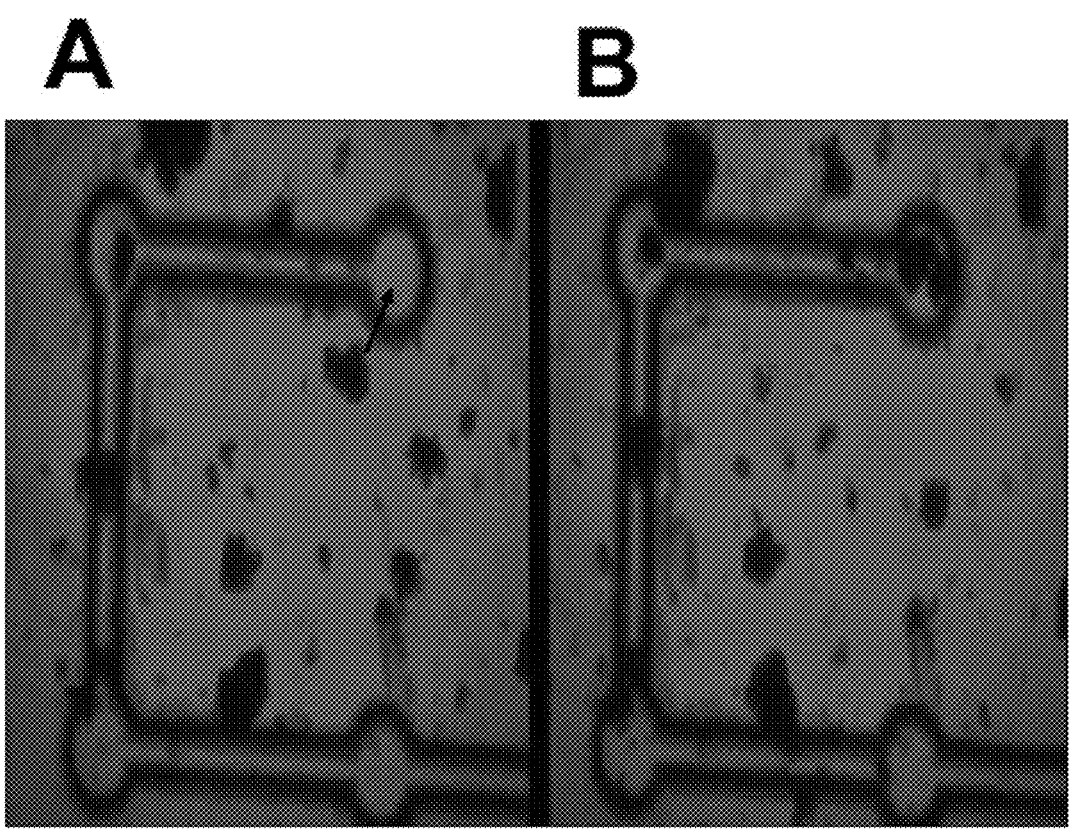

Some embodiments of the disclosure may provide cell patterning on a surface using current-carrying wires or permanent magnetic fields that attract cells to a pattern on the surface. Current carrying wires may be created in or on a surface or affixed in or on a surface or held in proximity above or below a surface by a variety of techniques. In some embodiments, lithographic patterning of conductive material on a surface may be used to make the wires. Sample patterns are illustrated in FIG. 16. An example of a force profile generated by such wires is illustrated in FIG. 17. A prototype of wires on a sapphire substrate, with tissue culture (also known as biological sample) wells above it is illustrated in FIG. 18. Photographs of the prototype, along with equipment to generate currents and incorporation into a microscope setup, are illustrated in FIG. 19. FIG. 20 illustrates currents passing through the wires to create a magnetic field that attracts cells and hydrogel containing MIO nanoparticles. Patterns of magnetic fields that can produce similar effects may also be produced with patterns of permanent magnetic material, such as bulk permanent magnets, patterns on magnetic recording tape, or patterns of materials such as used in magnetic data storage computer hard drives.

FIG. 16 illustrates a close-up of sample lithographic patterns for current carrying wires for making surface patterns of cells, according to embodiments of the disclosure. The 50 mm scale bar only applies to the top 3 forms.

FIG. 17 illustrates sample magnetic force calculations, applicable to some embodiments of the disclosure. Force profile may be normalized to current squared and magnet dipole moment for a cross-section across two parallel current-carrying wires 1 micron above the wires. MIO containing hydrogel and cells may be attracted to positions where the force crosses zero.

FIG. 18 illustrates prototype microdevice construction for lithographically patterned wires, according to embodiments of the disclosure. Current-carrying wires may be patterned using standard techniques of lithography, followed by electroplating of gold. Either a negative or positive photoresist may be used, where the resulting pattern is the inverse of the mask used. Shown in the left side of the figure are examples of the lithography mask. On the right side is a sapphire microscope slide with the lithographically patterned gold wires. On top of the slide is an array of plastic sample wells. Sapphire may be a good choice of substrate because it is optically transparent, electrically insulated, thermally conducting, optically polishable, and not susceptible to fracture upon local heating.

FIG. 19 illustrates a microscope set up and microchip device useful in some embodiments of the disclosure. The left side shows the microscope with a microchip. The right side shows a close-up of the chip, showing the electrical connections and plastic sample wells.

FIG. 20 illustrates manipulation and surface patterning of neural stem cells with patterning microdevice, according to embodiments of the disclosure. C17.2 murine neural stem cells may be cultured within hydrogel for 48 h. FIG. 20A illustrates no current being applied. FIG. 20B illustrates cell assemblies displaced towards the Au wire pattern when a 4 A current is applied. Here, the wires are below the plastic forming the container for the cells and media, so the cells are not in contact with wires. Cells in wells were still viable 48 hrs after the experiment was performed.

Yet another embodiment of the disclosure may utilize the same systems and methods to pattern on a surface Au-MIO-phage without cells, as illustrated in FIGS. 21-24.

Figure 21:
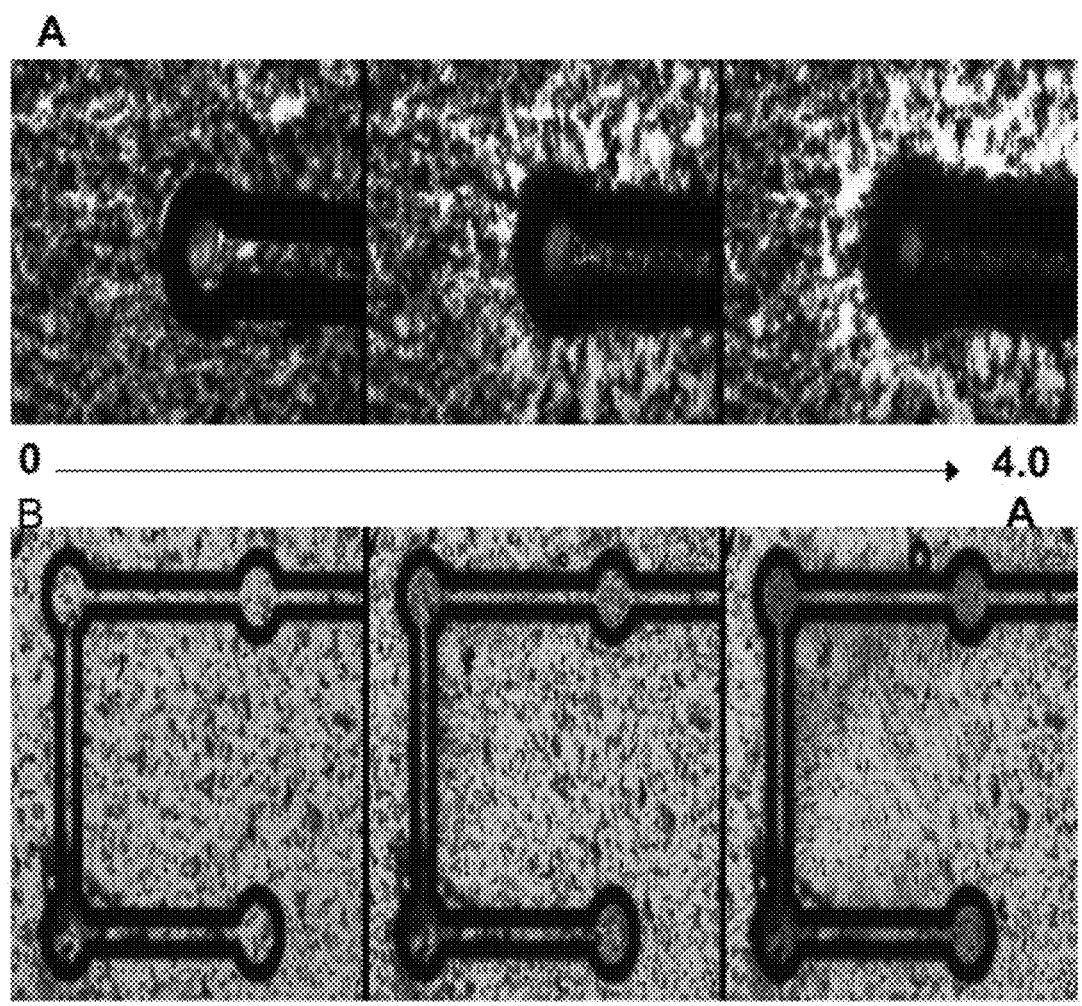

FIG. 21 illustrates the formation of patterns of Au-MIO-phage using current carrying wires to generate a patterned magnetic field. Similar patterns may be generated with permanent magnets, such as on magnetic recording tape, or with solid magnetic material, such as is used in computer hard drives. Levitated patterns may also be formed and manipulated. A gradient of Au-MIO-phage also may be formed by the creation of a gradient in the magnetic field, as illustrated in FIG. 22.

FIG. 21 illustrates manipulation and patterning of Au-MIO-phage material without cells, demonstrated with patterning microdevice, according to embodiments of the disclosure. Hydrogel patterning may be generated by applying current to lithographically patterned Au wires. This may move the hydrogel towards maxima of the magnetic field that are located between the wires or in the center of the loops. Both FIGS. 21A and 21B illustrate the sequences of no current being applied in the first frame, and the current ramped up to 4.0 A over an interval of 45 s, which produces patterns of the hydrogel shown in the far right pattern.

According to embodiments of the disclosure, the field may have a strength and gradient of sufficient strength to lift cell off the bottom surface of the culturing container, or collect the cells in suspension, or pull the cells to the surface, depending upon the desired effect. The cells may be levitated in the bulk of the media or brought to the air liquid interface where surface tension will keep the cells from leaving the liquid medium. To control the position of cells, the amount of magnetic material per cell and the strength and gradient of the magnetic field may be sufficient to overcome other forces on the cells that would disrupt patterning. This may be accomplished over a great range of parameters predicted by standard formulas, but the parameters may depend upon the specific embodiment of the disclosure. For example, for surface or levitated patterning and manipulating cells, at least 0.01 pg/cell of magnetite is needed. More magnetic material can be used, up to 100 mg/cell, which may produce more force. Material with larger or smaller magnetization would necessitate smaller or larger concentrations respectively. Typical magnetic fields on the order of 1G to 105 G and field gradients from 0.01 G/cm to 105 G may be used depending upon the application. Simple experimentation can be done to find the optimal conditions.

FIG. 22 illustrates a Au-MIO-phage gradient generation using a magnetic field gradient, according to embodiments of the disclosure, shown with brightfield photomicrograph (transmitted light) (scale bar, 20 µm). This image shows a change in transmitted light resulting from hydrogel gradient (higher density in dark region, indicated by arrow below the figure) generated from placing a permanent magnet next to the microwell in which Au—FeO nanoparticles solution was added to phage solution as part of hydrogel synthesis.

Cells may concentrate spontaneously in regions of high hydrogel concentration, so patterning the hydrogel first may provide another way to pattern cells, as illustrated in FIG. 23. Hydrogel may be formed with different kinds of phage without significantly altering the ability to form a hydrogel or incorporate magnetic nanopartcles. Phage may be designed with cell-specific receptors that preferentially bind to cells, such as phage expressing the RGD-4C peptide. A pattern of hydrogel Au-MIO-RGD-4C, formed in one embodiment with two permanent magnets beneath the culturing well, may lead to a patterning of Melanoma cells (B16) incubated for 16 hours (top, receptor mediated). Phage expressing fd-tet peptide may not bind to cells as strongly, so Au-MIO-fd-tet hydrogel may serve as a control (bottom, control). Two permanent magnets may be placed under each well, with magnetic fields pointed to opposite directions, so that the magnets repel each other. Hydrogel and nanoparticles may be uptaken and/or attached to cells through integrin binding peptide motif, which mediates cell adhesion, displayed on the phage. This may lead to more of a concentration of cells in areas of strong field near each magnet (indicated by the gap of cells between the magnets). In contrast, the control hydrogel (bottom) cells may cover the entire microwell.

FIG. 23 illustrates receptor-targeted cell patterning using magnetic field patterning of hydrogels, according to some embodiments of the disclosure. A hydrogel may be formed with different kinds of phage without significantly altering the ability to form a hydrogel or incorporate magnetic nanopartcles. Phage can be designed with cell-specific receptors that preferentially bind to cells, such as phage expressing the RGD-4C peptide. A pattern of hydrogel Au-MIO-RGD-4C formed in this case with two permanent magnets beneath the culturing well may lead to a patterning of Melanoma cells (B16) incubated for 16 hours (top, receptor mediated). Phage expressing fd-tet peptide may not bind to cells as strongly, so Au-MIO-fd-tet hydrogel may serve as a control (bottom, control). Two permanent magnets were placed under each well, with magnetic fields pointed to opposite directions (magnets repelled each other). The system where hydrogel and nanoparticles are uptaken and/or attached to cells through integrin binding peptide motif, which mediates cell adhesion, displayed on the phage leads to more of a concentration of cells in areas of strong field near each magnet (indicated by the gap of cells between the magnets). In contrast, the control hydrogel (bottom) cells covered the entire microwell.

Because phage may be modified to serve as a gene delivery vector, patterning the hydrogel may lead to patterned transfection of genetic material, as illustrated in FIG. 24. In some embodiments, adeno-virus associated virus phage (AAVP)[38] may be used to form Au-MIO-AAVP for superior gene delivery tools. The combination of AAVP with phage hydrogel may be a powerful tool for following the fate of the nanoparticles. Additionally, the combination may provide indications of where gene translation takes place and, for combination of multimodal imaging, magnetic guidance and gene/RNA delivery. Cells in the region with higher concentration of hydrogel may show a higher level of transfection, producing a patterned expression of the gene. This approach may also translate to delivery of small RNA guided towards gene silencing tools. This gene delivery capability may also be incorporated into any of the cell-patterning methods already discussed.

FIG. 24 illustrates magnetic-guided gene transfection using Au-MIO-AAVP, according to embodiments of the disclosure. Here, KS1767 cells are incubated with Au-MIO AAVP-RGD-4C. The Au-MIO AAVP-RGD-4C (AAVP, adeno-virus associated virus phage;)[38] may integrate targeting properties, and efficient gene transduction of phage-based vectors with magnetic guidance of hydrogels as a superior gene delivery tool. The left panel is brightfield image while the right is fluorescence image of GFP expressing cells. Within the same microwell, the line indicates the boundary dividing a region in which a magnet has concentrated the magnetic nanoparticle-carrying Au-MIO AAVP-RGD-4C (permanent magnet placed under the well), and region in which there is lower magnetic field and no concentration. The cells in the region with higher concentration of hydrogel may show transfection levels that are significantly (~6× greater).

Some embodiments may provide results which compare favorably with traditional methods. For example, culturing by magnetic levitation may provide favorable results when compared with established 3D cell culturing methods. A common 3D culturing matrix product is Matrigel,© commercially available from BD, Inc. Matrigel generally consists of purified basement membrane matrix, is derived from mouse, and is considered the "gold standard" for 3D cell assembly[7]. Cells dispersed in Matrigel may only form larger multicellular structures with significant cell-cell interactions after time has passed for sufficient cell migration and division. The Matrigel matrix may also produces high levels of diffraction, scattering, opacity, and auto-fluorescence, which are acknowledged difficulties in many established 3D cell culturing models based on extra-cellular matrices and polymeric gels/scaffolds.[2, 59] Matrigel may present additional limitations, including the need for serum-free conditions, which are not desirable for culturing most cells, and expensive growth factor supplements. Tissue grown in Matrigel may not be introduced in humans because mouse proteins may elicit an immune response. Finally, there is not potential for spatial or temporal manipulation of cells using Matrigel, while, as shown below, this is straightforward with magnetic levitation.

The present disclosure provides, in certain embodiments, a system comprising cells, a plurality of nanoparticles disposed within or attached onto or entrained in the cells, at least one type of which is magnetic, and a magnetic field created by current-carrying wires and/or permanent magnets which apply a force to at least one of the plurality of nanoparticles.

The present disclosure provides, in certain embodiments, a system comprising cells, a plurality of nanoparticles disposed within or attached onto or entrained in the cells, at least one type of which is magnetic, and a magnetic field created by current-carrying wires or permanent magnets which apply a force to at least one of the plurality of nanoparticles and brings the cells away from surface so as to grow in suspension in liquid media or at an gas-liquid interface. The cells are then allowed to grow while suspended.

The present disclosure provides, in certain embodiments, a system comprising cells, a plurality of nanoparticles disposed within or attached onto or entrained in the cells, at least one type of which is magnetic, and a magnetic field created by current-carrying wires or permanent magnets which apply a force to at least one of the plurality of nanoparticles and brings the cells away from surface so as to grow in suspension in liquid media or at an gas-liquid interface. The cells are then allowed to grow while suspended, and the magnetic field is altered so as to bring cells to a specific place on a surface, so that some cells will attach there. The field is then altered to allow cells to attach in another place to form a pattern.

The present disclosure provides, in certain embodiments, a system comprising cells, a plurality of nanoparticles disposed within or attached onto or entrained in the cells, at least one type of which is magnetic, and a magnetic field created by current-carrying wires or permanent magnets which apply a force to at least one of the plurality of nanoparticles and brings the cells toward a surface so as to grow in a specified pattern.

The present disclosure provides, in certain embodiments, a system comprising phage, a plurality of nanoparticles disposed within the phage, and a magnetic field created by current-carrying wires or permanent magnets which apply a force to at least one of the plurality of nanoparticles.

The present disclosure provides, in certain embodiments, a system comprising phage, a plurality of nanoparticles disposed within the phage, and one or more conductive wires, wherein at least a portion of the one or more wires is in contact with the phage.

The present disclosure provides, in certain embodiments, a method of fabricating a material, the method comprising: providing a material comprising phage, a plurality of nanoparticles, and one or more conductive wires, wherein at least a portion of the one or more wires is in contact with the phage, flowing an electric current through one or more of the one or more conductive wires so as to generate a magnetic field, and allowing the material to be altered in response to the magnetic field.

The present disclosure provides, in certain embodiments, a method for levitating a plurality of cells. The method may comprise providing a magnetic field. The method may also comprise levitating at least some of the plurality of cells in the magnetic field, wherein the plurality of cells comprise magnetic nanoparticles.

The present disclosure also provides, in some embodiments, a method of culturing cells. The method may comprise providing a plurality of cells. The method may also comprise providing a magnetic field. The method may also comprise levitating at least some of the plurality of cells in the magnetic field, wherein the plurality of cells comprise magnetic nanoparticles. The method may also comprise maintaining the levitation for a time sufficient to permit cell growth to form an assembly.

The present disclosure also provides, in other embodiments, a method of manipulating cells. The method may comprise providing a first plurality of cells. The method may also comprise providing a magnetic field. The method may also comprise levitating at least some of the first plurality of cells in the magnetic field, wherein the first plurality of cells comprise magnetic nanoparticles. The method may also comprise varying the magnetic field over time to manipulate at least a first portion of the first plurality of cells.

The present disclosure also provides, in particular embodiments, a method of preparing nanoparticles. The method may comprise providing a hydrogel comprising magnetic nanoparticles. The method may also comprise providing a magnetic field. The method may also comprise subjecting the hydrogel to the magnetic field.

The present disclosure also provides, in yet other embodiments, a system for levitating a plurality of cells. The system may comprise a magnetic field. The system may also comprise the plurality of cells, wherein the plurality of cells are disposed in the magnetic field, and the plurality of cells comprise magnetic nanoparticles.

To facilitate a better understanding of the present disclosure, the following examples of specific embodiments are given. In no way should the following examples be read to limit or define the entire scope of the disclosure.

EXAMPLES

A hydrogel assembly containing magnetic nanoparticles was formed as follows. Hydrogels were generated by described nanofabrication procedures[39, 40] except for the inclusion of MIO nanoparticles. A gold nanoparticle solution (50±8 nm diameter) was prepared following the common citrate-reduction[70] procedure (molar ratio of 0.8:1.0 of sodium citrate:Au(III) chloride; Sigma-Aldrich). MIO-containing hydrogels were prepared by mixing the gold nanoparticle solution (Optical absorbance 530 nm=1.2-1.5 units) with MIO nanopowder (specified as magnetite, polydisperse particle size <50 nm; stabilized with a surfactant of PVP (poly vinyl pyrrolidone); Sigma-Aldrich) to a concentration of 0.3 mg/ml. A phage dilution was prepared with 109 transducing units (TU)/μl in picopure water (H2O). Finally, the phage solution and the gold nanoparticle plus iron oxide solution were mixed with equal volumes and allowed to stand overnight at 4° C. for hydrogel formation. Prior to experimental use, each supernatant was shown to be nanoparticle-free as evidenced by light extinction measurements in the visible region, data indicative that all metal nanoparticles were incorporated into the resulting hydrogel.

Cells cultured in MIO-containing hydrogels were magnetically levitated as follows. Surface attached cells (grown to approximately 80% confluence) were treated with 1 μl of hydrogel per 1 cm2 of surface area available for culturing cells (size of culturing flask) and incubated overnight. The treated cells were de-attached by trypsin and EDTA. The trypsin was removed by centrifugation. The cells were placed into a tissue culture Petri dish.[39, 40] A cover top with an attached neodymium magnet was immediately put in place. The cell lines and corresponding culture media used were human glioblastoma-derived LN-229 or U-251MG cells (GFP and mCherry transfected) and normal human astrocytes (mCherry transfected) in Dulbecco modified Eagle's medium (DMEM) containing 10% fetal bovine serum (FBS) and in DMEM high-glucose 10% FBS supplemented with sodium pyruvate 2 mM, glutamine, penicillin, and streptomycin. C17.2 murine neural stem cells were cultured in DMEM high-glucose containing 10% FBS and supplemented with sodium pyruvate 2 mM glutamine, penicillin, and streptomycin.[71]

As illustrated in FIG. 12, cell viability and number of cells being used was assured after cells were de-attached. The cells were checked for viability with Trypan-blue exclusion and counted with a standard hemocytometer. In this same experiment, half of the cell population (~3×104) was transferred to seed a 2D surface-attached sample, and the other half was seeded to form a 3D-levitated assembly. Finally, the number of cells in the levitated multicellular structure was estimated by dividing the estimated volume of the structure (from its shape and size) by the average volume of a single cell (~1.0 nL).

FIG. 1 illustrates Magnetic Resonance Images, which were acquired with a 4.7 T, 40 cm Bruker Biospec MRI instrument. Hydrogels were placed in a 12 ml plastic conical tube for imaging.

As illustrated in FIGS. 4, 7, 8, 12, 13, 14,15, Bosc, NHA (normal human astrocytes) and the following human HGBM cell lines: LN229 and U251 were grown in Dulbecco modified Eagle's medium (DMEM) supplemented with 10% fetal calf serum (FCS). Transfections and retroviral infections were described. The m-cherry and eGFP in the retroviral vectors pCXb and pCXp, respectively, were transfected into Bosc cells to produce retrovirus containing supernatants which were collected 48 hr after the transfection and used for infection of the NHA, NSC, and GBM cells as previously described. The cells were treated and maintained in selection media 48 hr after infection: blasticidin (mCherry) or puromycin (eGFP) and express the fluorescent protein in a stable manner.

Multicellular assemblies of human glioblastoma cells were fixed in 10 mM PBS containing 1% glutaraldehyde after 24 h and 8 d of magnetic levitation. These structures were then placed on a nickel mesh grids previously coated with Formvar and evaporated with carbon were floated on drops of 0.1% poly-L-lysine (Sigma Diagnostics) on parafilm for 5 min. Excess solution was removed from the grid by carefully touching the edge of the grid onto filter paper. The grids were not allowed to dry completely in any of the steps. The grids were floated on drops of sample on parafilm for 1 h. Excess fluid was removed and the grids then were floated on drops of 0.02% BSA containing 1% ammonium molybdate in distilled water (pH 7.0) for 1 min. Excess fluid was removed, and the grids were allowed to dry overnight. Transmission electron microscopy images were captured by a transmission electron microscope (JEM-1010, JEOL) fitted with an AMT Advantage (Deben UK Limited, Suffolk, U.K.) digital charge-coupled device camera system.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

REFERENCES

1. Polak, J. M.; Mantalaris, S., Stem Cells Bioprocessing: An Important Milestone to Move Regenerative Medicine Research Into the Clinical Arena. Pediatr. Res. 2008, 63, (5), 461-466.
2. Cukierman, E.; Pankov, R.; Stevens, D. R.; Yamada, K. M., Taking Cell-Matrix Adhesions to the Third Dimension. Science 2001, 294, (5547), 1708-1712.
3. Atala, A., Advances in Tissue and Organ Replacement. Curr. Stem Cell Res. Ther. 2008, 3, (1), 21-31.
4. Abbott, A., Biology's new dimension. Nature 2003, 424, 870-872.
5. Kim, J. B.; Stein, R.; O'Hare, M. J., Three-dimensional in vitro tissue culture models of breast cancer—a review. Breast Cancer Res. Treat. 2004, 85, (3), 281-291.

6. Pampaloni, F.; Reynaud, E. G.; Stelzer, E. H. K., The third dimension bridges the gap between cell culture and live tissue. Nat. Rev. Mol. Cell Biol. 2007, 8, (10), 839-845.
7. Prestwich, G. D., Simplifying the extracellular matrix for 3-D cell culture and tissue engineering: A pragmatic approach. J. Cell. Biochem. 2007, 101, (6), 1370-1383.
8. Wang, R.; Xu, J.; Juliette, L.; Castilleja, A.; Love, J.; Sung, S. Y.; Zhau, H. E.; Goodwin, T. J.; Chung, L. W., Three-dimensional co-culture models to study prostate cancer growth, progression, and metastasis to bone. Semin. Cancer Biol. 2005, 15, (5), 353-364.
9. Boudreau, N.; Weaver, V., Forcing the Third Dimension. Cell 2006, 125, (3), 429-431.
10. Atala, A., Engineering tissues, organs and cells. J. Tissue Eng. Regen. Med. 2007, 1, (2), 83-96.
11. Griffith, L. G.; Swartz, M. A., Capturing complex 3D tissue physiology in vitro. Nat. Rev. Mol. Cell Biol. 2006, 7, (3), 211-224.
12. Friedrich, M. J., Studying Cancer in 3 Dimensions: 3-D Models Foster New Insights Into Tumorigenesis. JAMA 2003, 290, (15), 1977-1979.
13. Souza, G.; Arap, W.; Pasqualini, R. Method and Compositions Related to Phage-Nanoparticle Assemblies. 2006.
14. Ito, A.; Takizawa, Y.; Honda, H.; Hata, K.; Kagami, H.; Ueda, M.; Kobayashi, T., Tissue engineering using magnetite nanoparticles and magnetic force: heterotypic layers of cocultured hepatocytes and endothelial cells. Tissue Eng. 2004, 10, (5-6), 833-40.
15. Ito, A.; Ino, K.; Hayashida, M.; Kobayashi, T.; Matsunuma, H.; Kagami, H.; Ueda, M.; Honda, H., Novel methodology for fabrication of tissue-engineered tubular constructs using magnetite nanoparticles and magnetic force. Tissue Eng. 2005, 11, (9-10), 1553-61.
16. Ito, A.; Hayashida, M.; Honda, H.; Hata, K.; Kagami, H.; Ueda, M.; Kobayashi, T., Construction and harvest of multilayered keratinocyte sheets using magnetite nanoparticles and magnetic force. Tissue Eng. 2004, 10, (5-6), 873-80.
17. Ito, A.; Hibino, E.; Kobayashi, C.; Terasaki, H.; Kagami, H.; Ueda, M.; Kobayashi, T.; Honda, H., Construction and delivery of tissue-engineered human retinal pigment epithelial cell sheets, using magnetite nanoparticles and magnetic force. Tissue Eng. 2005, 11, (3-4), 489-96.
18. Srouji, S.; Kizhner, T.; Livne, E., 3D scaffolds for bone marrow stem cell support in bone repair. Regen. Med. 2006, 1, (4), 519-28.
19. Even-Ram, S.; Yamada, K. M., Cell migration in 3D matrix. Curr. Opin. Cell Biol. 2005, 17, (5), 524-32.
20. Ng, C. P.; Pun, S. H., A perfusable 3D cell-matrix tissue culture chamber for in situ evaluation of nanoparticle vehicle penetration and transport. Biotechnol. Bioeng. 2008, 99, (6), 1490-501.
21. Lin, A. Y.; Ai, Z.; Lee, S.-C.; Bajcsy, P.; Pe'er, J.; Leach, L.; Maniotis, A. J.; Folberg, R., Comparing Vasculogenic Mimicry With Endothelial Cell-lined Vessels: Techniques for 3D Reconstruction and Quantitative Analysis of Tissue Components from Archival Paraffin Blocks. Appl. Immunohistochem. Mol. Morphol. 2007, 15, (1), 113-9.
22. Zhang, S.; Gelain, F.; Zhao, X., Designer self-assembling peptide nanofiber scaffolds for 3D tissue cell cultures. Semin. Cancer Biol. 2005, 15, (5), 413-20.
23. Decaestecker, C.; Debeir, O.; Van Ham, P.; Kiss, R., Can anti-migratory drugs be screened in vitro? A review of 2D and 3D assays for the quantitative analysis of cell migration. Med. Res. Rev. 2007, 27, (2), 149-76.
24. Schindler, M.; Nur-E-Kamal, A.; Ahmed, I.; Kamal, J.; Liu, H.-Y.; Amor, N.; Ponery, A. S.; Crockett, D. P.; Grafe, T. H.; Chung, H. Y.; Weik, T.; Jones, E.; Meiners, S., Living in three dimensions: 3D nanostructured environments for cell culture and regenerative medicine. Cell Biochem. Biophys. 2006, 45, (2), 215-227.
25. Pankhurst, Q.; Connolly, J.; Jones, S. K.; Dobson, J., Applications of magnetic nanoparticles in biomedicine. J. Phys. D: Appl. Phys. 2003, 36, R167-R181.
26. Ino, K.; Ito, A.; Honda, H., Cell patterning using magnetite nanoparticles and magnetic force. Biotechnol. Bioeng. 2007, 97, (5), 1309-1317.
27. Ito, A.; Shinkai, M.; Honda, H.; Kobayashi, T., Medical application of functionalized magnetic nanoparticles. J. Biosci. Bioeng. 2005, 100, (1), 1-11.
28. Dobson, J., Remote control of cellular behaviour with magnetic nanoparticles. Nat. Nanotechnol. 2008, 3, (3), 139-143.
29. Au, C.; Mutkus, L.; Dobson, A.; Riffle, J.; Lalli, J.; Aschner, M., Effects of Nanoparticles on the Adhesion and Cell Viability on Astrocytes. Biol. Trace Elem. Res. 2007, 120, (1-3), 248-256.
30. Dobson, J.; Cartmell, S. H.; Keramane, A.; El Haj, A. J., Principles and design of a novel magnetic force mechanical conditioning bioreactor for tissue engineering, stem cell conditioning, and dynamic in vitro screening. IEEE Trans. Nanobioscience 2006, 5, (3), 173-7.
31. Hautot, D.; Pankhurst, Q. A.; Morris, C. M.; Curtis, A.; Burn, J.; Dobson, J., Preliminary observation of elevated levels of nanocrystalline iron oxide in the basal ganglia of neuroferritinopathy patients. Biochim. Biophys. Acta 2007, 1772, (1), 21-25.
32. Coleman, C. B.; Gonzalez-Villalobos, R. A.; Allen, P. L.; Johanson, K.; Guevorkian, K.; Valles, J. M.; Hammond, T. G., Diamagnetic levitation changes growth, cell cycle, and gene expression of *Saccharomyces cerevisiae*. Biotechnol. Bioeng. 2007, 98, (4), 854-863.
33. Winkleman, A.; Gudiksen, K. L.; Ryan, D.; Whitesides, G. M.; Greenfield, D.; Prentiss, M., A magnetic trap for living cells suspended in a paramagnetic buffer. Appl. Phys. Lett. 2004, 85, (12), 2411-2413.
34. Felder, R. A.; Gildea, J. J. Automated Cell Culture System and Process. 2003.
35. Becker, J. L.; Coffin, S. B. Magnetic Three-Dimensional Cell Culture Apparatus and Method. 2003.
36. Gillette, B. M.; Jensen, J. A.; Tang, B.; Yang, G. J.; Bazargan-Lari, A.; Zhong, M.; Sia, S. K., In situ collagen assembly for integrating microfabricated three-dimensional cell-seeded matrices. Nat. Mater. 2008, 7, (8), 636-40.
37. Lee, J.; Cuddihy, M. J.; Kotov, N. A., Three-Dimensional Cell Culture Matrices: State of the Art. Tissue Eng. Part B 2008, 14, (1), 61-86.
38. Hajitou, A.; Trepel, M.; Lilley, C. E.; Soghomonyan, S.; Alauddin, M. M.; Marini III, F. C.; Restel, B. H.; Ozawa, M. G.; Moya, C. A.; Rangel, R.; Sun, Y.; Zaoui, K.; Schmidt, M.; von Kalle, C.; Weitzman, M. D.; Gelovani, J. G.; Pasqualini, R.; Arap, W., A hybrid vector for ligand-directed tumor targeting and molecular imaging. Cell 2006, 125, (2), 385-98.
39. Souza, G. R.; Christianson, D. R.; Staquicini, F. I.; Ozawa, M. G.; Snyder, E. Y.; Sidman, R. L.; Miller, J. H.; Arap, W.; Pasqualini, R., Networks of Gold Nanoparticles and Bacteriophage as Biological Sensors and Cell-Targeting Agents. Proc. Natl. Acad. Sci. U.S.A. 2006, 103, (5), 1215-1220.

40. Souza, G. R.; Yonel-Gumruk, E.; Fan, D.; Easley, J.; Rangel, R.; Guzman-Rojas, L.; Miller, J. H.; Arap, W.; Pasqualini, R., Bottom-Up Assembly of Hydrogels from Bacteriophage and Au Nanoparticles: The Effect of Cis- and Trans-Acting Factors. PLoS ONE 2008, 3, (5), e2242.
41. Illés, E.; Tombácz, E., The effect of humic acid adsorption on pH-dependent surface charging and aggregation of magnetite nanoparticles. J. Colloid Interface Sci. 2006, 295, (1), 115-123.
42. Wan, X.; Li, Z.; Lubkin, S. R., Mechanics of mesenchymal contribution to clefting force in branching morphogenesis. Biomech. Model. Mechanobiol. 2008, 7, (5), 417-426.
43. Rosines, E.; Schmidt, H. J.; Nigam, S. K., The Effect of Hyaluronic Acid Size and Concentration on Branching Morphogenesis and Tubule Differentiation in Developing Kidney Culture Systems: Potential Applications to Engineering of Renal Tissues. Biomaterials 2007, 28, (32), 4806-4817.
44. Warheit, D. B.; Sayes, C. M.; Reed, K. L.; Swain, K. A., Health effects related to nanoparticle exposures: Environmental, health and safety considerations for assessing hazards and risks. Pharmacol. Ther. 2008, 120, (1), 35-42.
45. Teeguarden, J. G.; Hinderliter, P. M.; Orr, G.; Thrall, B. D.; Pounds, J. G., Particokinetics in vitro: dosimetry considerations for in vitro nanoparticle toxicity assessments. Toxicol. Sci. 2007, 95, (2), 300-312.
46. Groneberg, D. A.; Giersig, M.; Welte, T.; Pison, U., Nanoparticle-Based Diagnosis and Therapy. Curr. Drug Targets 2006, 7, (6), 643-648.
47. Kolonin, M. G.; Saha, P. K.; Chan, L.; Pasqualini, R.; Arap, W., Reversal of obesity by targeted ablation of adipose tissue. Nat. Med. 2004, 10, (6), 625-632.
48. Barbas III, C. F.; Burton, D. R.; Scott, J. K.; Silverman, G. J., Phage Display, A Laboratory Manual. Cold Spring Harbor Laboratory Press: New York, 2001.
49. Wang, X.-B.; Huang, Y.; Gascoyne, P. R. C.; Becker, F. F.; Hölzel, R.; Pethig, R., Changes in Friend murine erythroleukaemia cell membranes during induced differentiation determined by electrorotation. Biochim. Biophys. Acta, Biomembr. 1994, 1193, (2), 330-344.
50. Csikász-Nagy, A.; Battogtokh, D.; Chen, K. C.; Novak, B.; Tyson, J. J., Analysis of a generic model of eukaryotic cell-cycle regulation. Biophys. J. 2006, 90, (12), 4361-79.
51. Ofek, G.; Revell, C. M.; Hu, J. C.; Allison, D. D.; Grande-Allen, K. J.; Athanasiou, K. A., Matrix development in self-assembly of articular cartilage. PLoS ONE 2008, 3, (7), e2795.
52. Marx, U.; Sandig, V., Drug Testing In Vitro: Breakthroughs and Trends in Cell Culture Technology. Wiley-VCH: Weinheim, Germany, 2007.
53. Chuang, Y.-Y.; Tran, N. L.; Rusk, N.; Nakada, M.; Berens, M. E.; Symons, M., Role of synaptojanin 2 in glioma cell migration and invasion. Cancer Res. 2004, 64, (22), 8271-8275.
54. Kenny, P. A.; Lee, G. Y.; Myers, C. A.; Neve, R. M.; Semeiks, J. R.; Spellman, P. T.; Lorenz, K.; Lee, E. H.; Barcellos-Hoff, M. H.; Petersen, O. W.; Gray, J. W.; Bissell, M. J., The morphologies of breast cancer cell lines in three-dimensional assays correlate with their profiles of gene expression. Mol. Oncol. 2007, 1, (1), 84-96.
55. Bhowmick, D. A.; Zhuang, Z.; Wait, S. D.; Weil, R. J., A Functional Polymorphism in the EGF Gene Is Found with Increased Frequency in Glioblastoma Multiforme Patients and Is Associated with More Aggressive Disease. Cancer Res. 2004, 64, (4), 1220-1223.
56. Nieder, C.; Astner, S. T.; Molls, M.; Grosu, A. L., Analysis of long-term survivors of glioblastoma multiforme in a single institution with aggressive local retreatment protocol. Anticancer Res. 2007, 27, (4C), 2993-2996.
57. Balakrishnan, A.; Bleeker, F. E.; Lamba, S.; Rodolfo, M.; Daniotti, M.; Scarpa, A.; van Tilborg, A. A.; Leenstra, S.; Zanon, C.; Bardelli, A., Novel Somatic and Germline Mutations in Cancer Candidate Genes in Glioblastoma, Melanoma, and Pancreatic Carcinoma. Cancer Res. 2007, 67, (8), 3545-3550.
58. Sanson, M.; Marcaud, V.; Robin, E.; Valéry, C.; Sturtz, F.; Zalc, B., Connexin 43-mediated bystander effect in two rat glioma cell models. Cancer Gene Ther. 2002, 9, (2), 149-155.
59. Yamada, K. M.; Cukierman, E., Modeling tissue morphogenesis and cancer in 3D. Cell 2007, 130, (4), 601-10.
60. Heyneman, A.; Beele, H.; Vanderwee, K.; Defloor, T., A systematic review of the use of hydrocolloids in the treatment of pressure ulcers. J. Clin. Nurs. 2008, 17, (9), 1164-73.
61. Cui, F. Z.; Tian, W. M.; Hou, S. P.; Xu, Q. Y.; Lee, I. S., Hyaluronic acid hydrogel immobilized with RGD peptides for brain tissue engineering. J. Mater. Sci. Mater. Med. 2006, 17, (12), 1393-401.
62. Burd, A., Evaluating the use of hydrogel sheet dressings in comprehensive burn wound care. Ostomy Wound Manage 2007, 53, (3), 52-62.
63. Park, H.; Temenoff, J. S.; Tabata, Y.; Caplan, A. I.; Mikos, A. G., Injectable biodegradable hydrogel composites for rabbit marrow mesenchymal stem cell and growth factor delivery for cartilage tissue engineering. Biomaterials 2007, 28, (21), 3217-27.
64. Mikos, A. G.; Herring, S. W.; Ochareon, P.; Elisseeff, J.; Lu, H. H.; Kandel, R.; Schoen, F. J.; Toner, M.; Mooney, D.; Atala, A.; Van Dyke, M. E.; Kaplan, D.; Vunjak-Novakovic, G., Engineering Complex Tissues. Tissue Eng. 2006, 12, (12), 3307-3339.
65. Ferreira, L. S.; Gerecht, S.; Fuller, J.; Shieh, H. F.; Vunjak-Novakovic, G.; Langer, R., Bioactive hydrogel scaffolds for controllable vascular differentiation of human embryonic stem cells. Biomaterials 2007, 28, (17), 2706-17.
66. Calvert, P., Materials science. Printing cells. Science 2007, 318, (5848), 208-9.
67. Prieve, D. C.; Alexander, B. M., Hydrodynamic Measurement of Double-Layer Repulsion Between Colloidal Particle and Flat Plate. Science 1986, 231, (4743), 1269-1270.
68. Ramachandran, N.; Hainsworth, E.; Bhullar, B.; Eisenstein, S.; Rosen, B.; Lau, A. Y.; Walter, J. C.; LaBaer, J., Self-assembling protein microarrays. Science 2004, 305, (5680), 86-90.
69. Arap, W.; Pasqualini, R.; Ruoslahti, E., Chemotherapy targeted to tumor vasculature. Curr. Opin. Oncol. 1998, 10, (6), 560-5.
70. Handley, D. A., Methods for synthesis of colloidal gold. In Colloidal Gold: Principles, Methods, and Applications, Hayat, M. A., Ed. Academic Press: San Diego, 1989; Vol. 1, pp 23-27.
71. Snyder, E. Y.; Deitcher, D. L.; Walsh, C.; Arnold-Aldea, S.; Hartweig, E. A.; Cepko, C. L., Multipotent neural cell lines can engraft and participate in development of mouse cerebellum. Cell 1992, 68, (1), 33-51.

The invention claimed is:
1. A method of 3D cell culture, comprising:
   a. providing a magnetic field gradient of at least 0.01 G/cm;
   b. providing cells and a hydrogel which comprises one or more magnetic nanoparticles, wherein said cells uptake said magnetic nanoparticles to become magnetic cells; and
   c. levitating at least some of the magnetic cells in the magnetic field gradient for a time sufficient to permit at least some of the magnetic cells to form a levitated 3D cell assembly, wherein the shape of said 3D cell assembly is controlled by controlling the shape of the magnetic field.

2. The method of claim 1, wherein the 3D cell assembly is formed through cell growth.

3. The method of claim 1, wherein the magnetic field is at least partially formed by one or more electromagnets, permanent magnets, or both.

4. The method of claim 1, wherein the cells comprise more than one cell type.

5. The method of claim 1, further comprising providing a feeding layer of cells, wherein the at least some of the magnetic cells are levitated proximate to the feeding layer.

6. The method of claim 1, further comprising introducing at least a portion of the 3D cell assembly into a living organism.

7. The method of claim 1, further comprising:
   a. adding a chemical to the 3D cell assembly;
   b. measuring an effect of said chemical on said 3D cell assembly; and
   c. projecting the effect of the chemical on an in vivo tissue based on the effect of the chemical on the 3D cell assembly.

8. The method of claim 1, wherein the magnetic nanoparticles are disposed inside said cells.

9. The method of claim 1, wherein the magnetic nanoparticles are attached to said cells.

10. The method of claim 1, wherein said hydrogel comprises Au-MIO-phage.

11. The method of claim 1, wherein at least some of the magnetic cells are levitated in the bulk volume of a liquid.

12. The method of claim 1, wherein at least some of the magnetic cells are levitated at a gas-liquid interface.

* * * * *